US012653527B2

(12) United States Patent
Haas

(10) Patent No.: US 12,653,527 B2
(45) Date of Patent: Jun. 16, 2026

(54) DEVICES AND METHODS FOR MINIMALLY INVASIVE SURGICAL PROCEDURES

(71) Applicant: NICE Surgical Solutions PTE. LTD., Singapore (SG)

(72) Inventor: Eric Haas, Houston, TX (US)

(73) Assignee: NICE Surgical Solutions Pte. Ltd., Singapore (SG)

( * ) Notice: Subject to any disclaimer, the term of this patent is extended or adjusted under 35 U.S.C. 154(b) by 1009 days.

(21) Appl. No.: 17/285,562

(22) PCT Filed: Oct. 19, 2019

(86) PCT No.: PCT/US2019/057098
§ 371 (c)(1),
(2) Date: Apr. 15, 2021

(87) PCT Pub. No.: WO2020/082052
PCT Pub. Date: Apr. 23, 2020

(65) Prior Publication Data
US 2021/0393259 A1      Dec. 23, 2021

Related U.S. Application Data

(60) Provisional application No. 62/747,809, filed on Oct. 19, 2018.

(51) Int. Cl.
A61B 17/04          (2006.01)
A61B 17/00          (2006.01)
(Continued)

(52) U.S. Cl.
CPC ........ A61B 17/0487 (2013.01); A61B 17/105 (2013.01); A61B 17/1114 (2013.01);
(Continued)

(58) Field of Classification Search
CPC ............ A61B 17/1114; A61B 17/0487; A61B 17/1155; A61B 2017/0488;
(Continued)

(56) References Cited

U.S. PATENT DOCUMENTS

| | | | | |
|---|---|---|---|---|
| 5,437,682 A | * | 8/1995 | Grice ................. | A61B 17/0469 606/205 |
| 5,484,451 A | * | 1/1996 | Akopov ................. | A61B 17/04 227/176.1 |

(Continued)

FOREIGN PATENT DOCUMENTS

| | | | | |
|---|---|---|---|---|
| CN | 104434243 A | * | 3/2015 | ....... A61B 17/07207 |

OTHER PUBLICATIONS

International Search Report for corresponding application PCT/US2019/057098 filed Oct. 19, 2019; Mail date Feb. 11, 2020.
(Continued)

*Primary Examiner* — Darwin P Erezo
*Assistant Examiner* — Mitchell Brian Hoag
(74) *Attorney, Agent, or Firm* — Offit Kurman; Christopher I. Halliday

(57)          ABSTRACT

A suture clip applier for applying a suture around a tubular tissue adjacent to an open lumen. The suture clip applier includes an elongated body having a tissue clinching mechanism at one end of the body. The tissue clinching mechanism comprises two arms that are movable between open and clinched positions. The suture clip applier includes a plurality of deformable suture clips mounted along a longitudinal length of the elongated body, wherein each suture clip is configured to be detachably positioned within an interior of the two arms and to be deformed between open and clinched positions in response to the two arms being moved between the open and clinched positions. The suture clip applier further includes a length of suture comprising a (Continued)

pre-formed adjustable fastening and a loop extending from the pre-formed adjustable fastening, the loop extending between the two arms.

12 Claims, 32 Drawing Sheets

(51) Int. Cl.

| | |
|---|---|
| *A61B 17/10* | (2006.01) |
| *A61B 17/11* | (2006.01) |
| *A61B 17/115* | (2006.01) |
| *A61B 17/29* | (2006.01) |
| *A61B 17/072* | (2006.01) |

(52) U.S. Cl.
CPC .......... *A61B 17/1155* (2013.01); *A61B 17/29* (2013.01); *A61B 2017/0488* (2013.01); *A61B 2017/07285* (2013.01)

(58) Field of Classification Search
CPC .............. A61B 17/0483; A61B 17/115; A61B 17/1152; A61B 2017/1157; A61B 2017/111; A61B 2017/1125; A61B 17/0469; A61B 2018/00494
USPC ......................................................... 606/143
See application file for complete search history.

(56) References Cited

U.S. PATENT DOCUMENTS

| | | | | |
|---|---|---|---|---|
| 5,490,856 | A * | 2/1996 | Person | A61B 17/072 606/151 |
| 5,520,702 | A * | 5/1996 | Sauer | A61B 17/0469 606/139 |
| 5,540,375 | A * | 7/1996 | Bolanos | A61B 17/072 227/19 |
| 5,669,918 | A | 9/1997 | Balazs | |
| 5,766,188 | A * | 6/1998 | Igaki | A61B 17/07207 606/139 |
| 6,159,224 | A * | 12/2000 | Yoon | A61B 18/1445 606/147 |
| 10,182,806 | B2 * | 1/2019 | Foerster | A61B 17/0401 |
| 11,090,038 | B2 * | 8/2021 | Balboa | A61B 17/8861 |
| 2003/0125734 | A1 * | 7/2003 | Mollenauer | A61B 18/085 606/51 |
| 2004/0092960 | A1 * | 5/2004 | Abrams | A61B 17/1152 606/139 |
| 2008/0249544 | A1 * | 10/2008 | Brand | A61B 17/0469 606/144 |
| 2009/0192352 | A1 * | 7/2009 | P. Regadas | A61B 17/3462 604/167.03 |
| 2011/0028997 | A1 * | 2/2011 | Gregoire | A61B 17/0401 606/144 |
| 2012/0037686 | A1 * | 2/2012 | Hessler | A61B 17/0482 606/232 |
| 2012/0080332 | A1 | 4/2012 | Shelton | |
| 2012/0239010 | A1 * | 9/2012 | Shelton, IV | A61B 17/07207 606/1 |
| 2012/0241505 | A1 * | 9/2012 | Alexander, III | A61B 17/1155 227/179.1 |
| 2013/0023905 | A1 * | 1/2013 | Kubalak | A61B 17/0482 606/144 |
| 2014/0131418 | A1 * | 5/2014 | Kostrzewski | A61B 17/07292 227/176.1 |
| 2014/0309666 | A1 * | 10/2014 | Shelton, IV | A61B 17/07207 606/139 |
| 2016/0100837 | A1 * | 4/2016 | Huang | A61B 17/32 227/176.1 |
| 2016/0213377 | A1 | 7/2016 | Shankarsetty | |
| 2016/0302793 | A1 * | 10/2016 | Fung | A61B 17/0487 |
| 2017/0086847 | A1 * | 3/2017 | DiNardo | A61B 17/105 |
| 2019/0261991 | A1 * | 8/2019 | Beckman | A61B 17/115 |
| 2020/0100790 | A1 * | 4/2020 | DiNardo | A61B 17/07207 |
| 2022/0183677 | A1 * | 6/2022 | Shattuck | A61B 17/0482 |

OTHER PUBLICATIONS

Written Opinion for corresponding application PCT/US2019/057098 filed Oct. 19, 2019; Mail date Feb. 11, 2020.

* cited by examiner

DEVICES AND METHODS FOR MINIMALLY INVASIVE SURGICAL PROCEDURES

CROSS-REFERENCE TO RELATED APPLICATIONS

This application claims the benefit of U.S. Provisional Patent Application No. 62/747,809 filed Oct. 19, 2018 entitled "Devices and Methods for Minimally Invasive Surgical Procedures", which is incorporated by reference herein in its entirety.

FIELD OF THE INVENTION

The present application relates to minimally invasive surgical methods, and devices for performing those methods. In particular, embodiments of the present invention relate to devices and methods for performing resection of a diseased segment of a colon and/or rectum, and extraction of the diseased segment through the rectum.

BACKGROUND OF THE INVENTION

Surgery in which a diseased portion of the intestine requires resection is common and is performed for a multitude of diseases including colorectal cancer, polyps, diverticulitis, Crohn's Disease, ulcerative colitis, rectal prolapse, endometriosis and others. The purpose of such a procedure is to remove the diseased portion of the intestine, preserve the normal portions of the bowel and perform a primary anastomosis to restore bowel continuity. Laparoscopic and robotic surgery, typically referred to as minimally invasive surgery (MIS), are approaches in which the procedure is performed with a camera and instruments placed through small ports in the abdomen ranging from approximately 5 mm to approximately 12 mm in diameter, and allow visualization, access and exposure and surgical maneuvers in the body cavity without making an open or large incision.

There are many benefits of MIS over traditional open surgery, including smaller incisions and abdominal wall trauma, reduced post-operative pain, reduced opioid consumption, earlier return of bowel function, fewer complications, lower length of hospital stay, and earlier return to activities of daily living. Currently, colorectal MIS typically requires placement of 4 or 5 ports through the abdominal wall for minimally invasive instruments and camera. For example, conventional laparoscopic surgery requires between approximately 5-approximately 12 mm diameter ports depending on the size of the camera and instruments. In cases in which a diseased segment of the alimentary track needs to be removed, one major drawback of the current mainstream laparoscopic and robotic techniques is the utilization of an additional abdominal wall incision. This incision typically ranges from 5 to 8 cm in length, which may double the cumulative incision size of the ports. The additional incision allows the surgeon to remove the diseased segment and perform all or portions of the bowel anastomosis directly through this incision.

Currently, nearly all laparoscopic and robotic procedures are performed with the utilization of this additional incision. The overwhelming majority of current practices do not utilize natural-orifice assisted methods to remove the specimen, nor do they attempt to overcome the cumbersome challenges of achieving a safe and successful intracorporeal anastomosis (ICA). Current methods utilize the abdominal wall incision to perform several surgical steps to prepare the bowel for the anastomosis. To accomplish these steps, the portion of the bowel designated for anastomosis is delivered outside the body through the abdominal wall incision in order to place and secure the anvil of the circular stapler. Thus, the laparoscopic or robotic portion of the procedure is interrupted to place an abdominal incision of several centimeters in length through which the specimen is extracorporealized. Once outside the body cavity, the bowel is divided at a margin of resection and the specimen is removed.

There are many disadvantages to bringing a portion of the bowel outside the body cavity, including the possibility of trauma or traction injury to the bowel wall or associated blood vessels, inability for the end of the bowel to reach the abdominal wall in certain anatomical situations, and potential for contamination of the incision with bowel contents, thereby increasing the risk of surgical site infections.

The placement and utilization of an additional transabdominal incision also carries numerous disadvantages and significantly adds to the invasiveness of the procedure. For example, such an incision may result in interruption of the flow of the procedure, as the introduction of an incision results in loss of pneumoperitoneum and therefore the minimally invasive platform is paused. In the case of laparoscopic surgery, the camera must be placed on standby and the instruments must be removed. In robotic surgery, one or more robotic arms must be completely undocked from the patient to gain access and exposure. There is also potential for contamination of the abdominal wall incision, traction injury of the bowel, inadequate resection of the specimen, additional procedure time, increased post-operative pain, increased need for opioid use, and increased morbidity rates.

There is therefore a need to develop methods and devices that facilitate minimally invasive colorectal procedures in which the resection, removal of the disease and formation of the anastomosis can be performed without requiring an incision on the abdominal wall or manipulation of bowel outside the body cavity.

BRIEF SUMMARY OF THE INVENTION

Embodiments of the present invention provide surgical devices for use in surgery, such as natural orifice assisted surgery using laparoscopic or robotic systems.

Embodiments of the present invention provide a suture clip applier for applying a suture around a tubular tissue adjacent to an open lumen, the suture clip applier comprising an elongated body comprising a tissue clinching mechanism at one end of the body, the tissue clinching mechanism comprising two arms that are movable between open and clinched positions, a plurality of deformable suture clips mounted along a longitudinal length of the elongated body, wherein each suture clip is configured to be detachably positioned within an interior of the two arms and to be deformed between open and clinched positions in response to the two arms being moved between the open and clinched positions. A length of suture comprises a pre-formed adjustable fastening and a loop extending from the pre-formed adjustable fastening, wherein the loop is configured to extend between the two arms of the suture clip applier.

According to particular embodiments, the suture clip applier includes a biasing element configured to longitudinally advance each deformable suture clip toward the tissue clinching mechanism. According to particular embodiments, the biasing element comprises one or more springs.

According to particular embodiments, the two arms are hinged to the elongated body of the clip applier.

According to particular embodiments, the suture clip applier includes between 4-20 deformable suture clips deformable suture clips, are mounted along the longitudinal length of the elongated body.

According to particular embodiments, the biasing element is configured to automatically advance each deformable suture clip toward the tissue clamping mechanism in response to a deformable suture clip being released from the clinching mechanism.

According to particular embodiments, a method of using the suture clip applier to apply a suture adjacent to an open lumen in a tubular tissue, comprises sequentially affixing a series of the deformable suture clips around the open lumen by actuating the tissue clinching mechanism to clinch each deformable suture clip onto the tubular tissue at a plurality of positions around the open lumen, the suture extending through the deformable suture clips affixed to the tubular tissue and forming a loop therethrough.

According to particular embodiments, the method includes using a cutting element (e.g., a pair of scissors, a surgical stapler, or the like) to divide the tubular tissue and expose the open lumen prior to affixing the series of deformable suture clips.

According to particular embodiments, the method includes tightening the suture around the open lumen.

Embodiments of the present invention provide a surgical device for placing a suture around a bowel or other tubular tissue, the surgical device comprising a first arm and a second arm each having a longitudinal length with opposite proximal and distal end portions, at least one of said first arm and said second arm being movable between an open position and a clamped position. The surgical device includes a suturing mechanism comprising a first row of suture staples positioned along the longitudinal length in said first arm, and optionally a second row of suture staples positioned along the longitudinal length in said second arm; and a length of suture comprising first and second end regions coupled together by a pre-formed adjustable fastening. A first threaded region of the suture extends through the first row of suture staples, and a second threaded region of the suture may extend through the second row of suture staples.

According to particular embodiments, the length of suture includes a first unthreaded region extending along the longitudinal length of the first arm, and a second unthreaded region extending along the longitudinal length of the second arm wherein when the suture is detached from the surgical device, the suture is biased to become unbent at the first and second bends such that the suture forms a loop extending from the pre-formed adjustable fastening.

According to particular embodiments, the first threaded region and the first unthreaded region of the suture are detachably coupled to the first arm, the second threaded region and the second unthreaded region of the suture are detachably coupled to the second arm, and the first and second end portions of the suture extend away from the first and second arms.

According to particular embodiments, the surgical device includes a suturing mechanism comprises a pushing mechanism configured to push the suture staples out of the interior portion when the suturing mechanism is actuated.

According to particular embodiments, the surgical device includes a cutting mechanism comprises a groove extending along the longitudinal length of the first or second arm, and the cutting element comprises a knife blade movably disposed in the groove and configured to move along said longitudinal length.

According to particular embodiments, the surgical device includes a stapling mechanism having staples positioned along the longitudinal length of the first arm or the second arm, and an anvil positioned along the longitudinal length of the other of the first arm or the second arm.

According to particular embodiments, the cutting mechanism is positioned along the longitudinal length between the suturing mechanism and the stapling mechanism.

According to particular embodiments, the stapling mechanism, the suturing mechanism and the cutting mechanism are configured to be actuated simultaneously or substantially simultaneously.

According to particular embodiments, a method of using the surgical system according to embodiments described above to apply a suture around a tubular tissue comprises: clamping the tubular tissue between the first arm and the second arm, actuating the cutting mechanism to divide the tubular tissue, thereby creating an open lumen, and actuating the suturing mechanism to attach the first and second rows of suture staples to the tubular tissue adjacent to the open lumen, wherein the suture comprising the pre-formed adjustable fastening detaches from the surgical device and forms a loop around the tubular tissue, with a portion of the suture extending through the suture staples.

According to particular embodiments, the method includes tightening the suture around the tubular tissue by pulling one or more of the first and second end portions of the suture.

A method of using the surgical system to intracorporeally resect a bowel specimen from a subject comprises clamping the first arm and the second arm over a proximal margin of resection between the specimen and a healthy bowel portion, actuating the cutting mechanism to divide the bowel at the proximal margin of resection, actuating the stapling mechanism to close an interior lumen of the specimen by applying the staples to a proximal edge portion of the specimen, actuating the suturing mechanism to attach the first and second rows of suture staples to an edge portion of the proximal bowel portion, wherein the suture comprising the pre-formed adjustable fastening detaches from the surgical device and forms a loop around the edge portion of the proximal bowel portion, a portion of the suture extending through the suture staples.

According to particular embodiments, the method includes clamping the first arm and the second arm over a distal margin of resection between the specimen and a healthy bowel portion, actuating the cutting mechanism to divide the bowel at the distal margin of resection, actuating the stapling mechanism to close an interior lumen of the specimen by applying the staples to a distal edge portion of the specimen, and actuating the suturing mechanism to attach the first and second rows of suture staples to an edge portion of the distal bowel portion, wherein the suture comprising the pre-formed adjustable fastening detaches from the surgical device and forms a loop around the edge portion of the distal bowel portion, a portion of the suture extending through the suture staples.

According to particular embodiments, the method includes actuating the cutting mechanism, actuating the stapling mechanism and actuating the suturing mechanism occur simultaneously, or substantially simultaneously, in response to a single actuation by a surgeon.

According to particular embodiments, the method includes extracting the specimen through the subject's rectum.

According to particular embodiments, the method includes extracting the specimen through the subject's rectum comprises transanally inserting a grasping tool through the distal bowel portion, grasping the specimen with the grasping tool and extracting the specimen through the subject's rectum.

According to particular embodiments, the method includes intracorporeally forming the anastomosis comprises transanally inserting a circular stapler and advancing the circular stapler through the distal bowel portion, the circular stapler comprising a stapling cartridge and an anvil component removably coupled thereto.

Embodiments of the present invention provide a transrectal extractor configured to expand a luminal circumference of a rectum, the transrectal extractor comprising a substantially cylindrical body comprising a deformable material extending along a longitudinal axis, the substantially cylindrical body having an exterior, an interior, and a top edge portion defining an opening into the interior, an optional drawstring extending through the interior and coupled to the top edge portion, and an optional external sheath slidably coupled to and surrounding at least a portion of the exterior of the substantially cylindrical body. According to particular embodiments, the substantially cylindrical body is configured to be positioned within the rectal lumen (e.g., extending longitudinally from an opening in the lumen, where the bowel has been divided, to the anal orifice or beyond the anal orifice), and to expand outward, thereby increasing its circumference and expanding the luminal circumference of the rectum.

According to particular embodiments, a method of using the transrectal extractor intracorporeally remove a specimen from a subject comprises transanally inserting the transrectal extractor through a distal bowel portion, and expanding the top edge portion around an opening in the distal bowel portion.

According to particular embodiments, the method includes transanally inserting a grasping tool through the transrectal retractor, grasping the specimen, and transanally extracting the specimen through the interior of the transrectal retractor.

According to particular embodiments, the method includes removing the transrectal extractor by pulling the drawstring (e.g., which inverts the top edge portion), thereby pulling the substantially cylindrical body out of the rectum.

Embodiments of the present invention provide a method of intracorporeally resecting a specimen from a subject comprises (1) separating the specimen from a bowel wall by: dividing the bowel wall at a proximal margin of resection, closing a proximal interior lumen of the specimen by applying staples to a proximal edge portion of the specimen, placing a suture around an edge portion of the proximal bowel portion; dividing the bowel wall at a distal margin of resection, closing a distal interior lumen of the specimen by applying staples to a distal edge portion of the specimen, placing a suture around an edge portion of the distal bowel portion; (2) extracting the specimen through the subject's rectum; and (3) intracorporeally forming an anastomosis between the proximal bowel portion and the distal bowel portion.

According to particular embodiments, the method does not include making an abdominal wall incision, except for port incisions.

According to particular embodiments, the method includes using a surgical device according to embodiments described herein to separate the specimen from the bowel wall, the surgical device comprising a first arm and a second arm each having a longitudinal length with opposite proximal and distal end portions, at least one of said first arm and said second arm being movable between an open position and a clamped position, a cutting mechanism comprising a cutting element, a suturing mechanism comprising a length of suture comprising first and second end regions coupled together by a pre-formed adjustable fastening, a first threaded region of the suture extending through a first row of suture staples positioned along the longitudinal length in said first arm, and a second threaded region of the suture extending through a second row of suture staples positioned along the longitudinal length in said second arm, and optionally a stapling mechanism comprising staples positioned along the longitudinal length of the first arm or the second arm, and an anvil positioned along the longitudinal length of the other of the first arm or the second arm.

According to particular embodiments, the method includes using a transrectal extractor to extract the specimen, the transrectal extractor comprising a substantially cylindrical body comprising a deformable material extending along a longitudinal axis, the substantially cylindrical body having an exterior, an interior, and a top edge portion defining an opening into the interior, an optional drawstring extending through the interior and coupled to the top edge portion, an optional external sheath slidably coupled to and surrounding at least a portion of the exterior of the substantially cylindrical body, the substantially cylindrical body being configured to expand outward and increase the opening's circumference, thereby expanding the luminal circumference of the rectum.

BRIEF DESCRIPTION OF THE DRAWINGS

The foregoing summary, as well as the following detailed description of embodiments of the minimally invasive surgical methods, and devices for performing those methods will be better understood when read in conjunction with the appended drawings of exemplary embodiments. It should be understood, however, that the invention is not limited to the precise arrangements and instrumentalities shown.

In the drawings.

DETAILED DESCRIPTION OF EXEMPLARY EMBODIMENTS OF THE INVENTION

Figure 1:
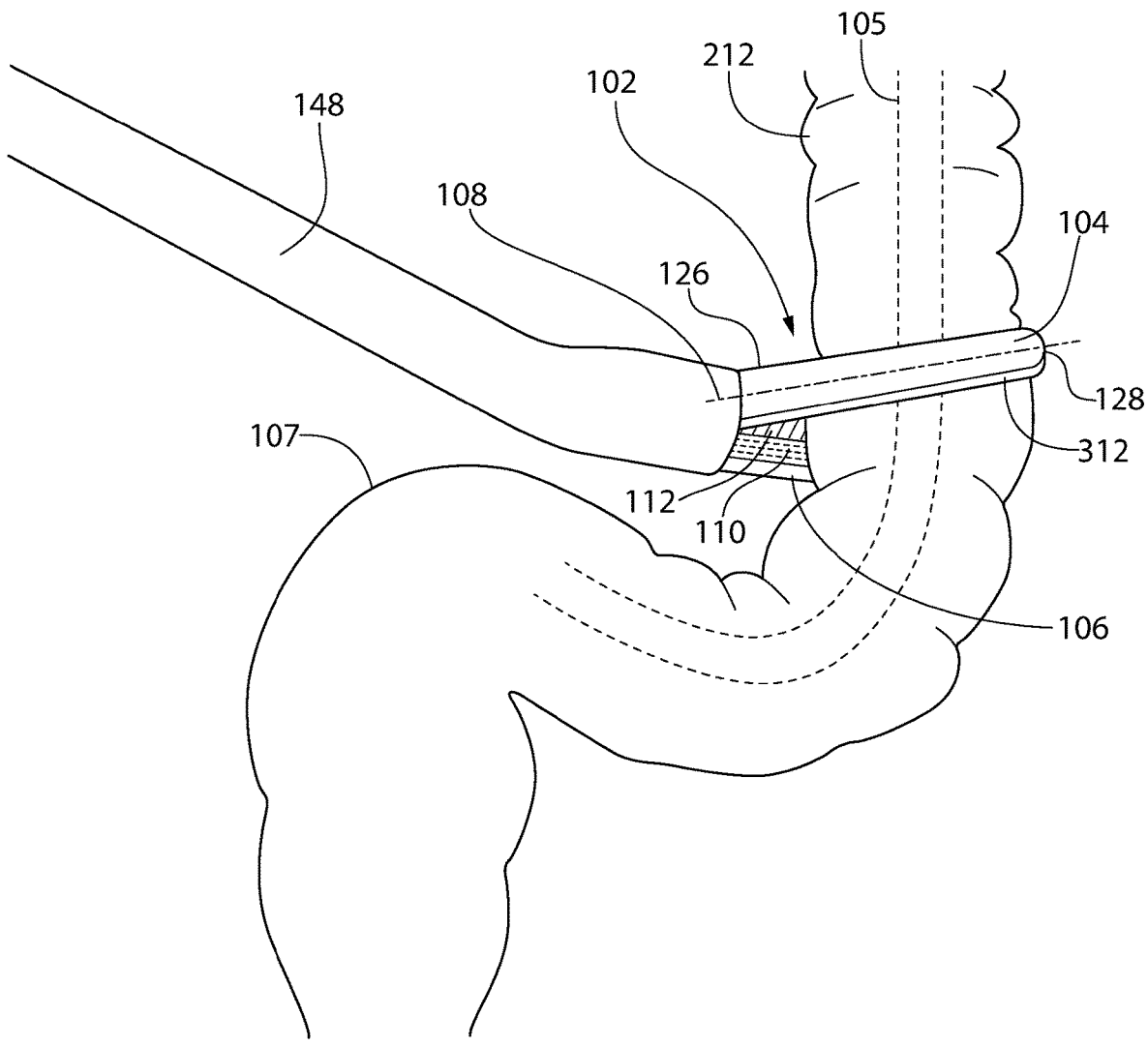
FIG. 1 is an illustration of a bowel wall being divided at a proximal margin of resection by a surgical device in accordance with an exemplary embodiment of the present invention.

Embodiments of the present invention relate to minimally invasive methods for the intracorporeal resection of a segment of tubular tissue, and devices for performing those methods. In particular, embodiments of the present invention relate to minimally invasive methods for performing colorectal resection. For example, embodiments of the present invention relate to devices and methods for the intracorporeal resection of a segment of a colon and/or rectum, extraction of the segment through the colon/rectum, and formation of an intracorporeal anastomosis (ICA) without the need for an abdominal wall incision, except for incisions needed for laparoscopic or robotic ports.

Embodiments of the present invention facilitate the ICA by using a device that applies a suture (e.g., a pursestring suture as discussed below) with a pre-formed adjustable fastening (e.g., pre-formed knot) to a bowel wall, which allows for tightening and closure of the suture without the need to laparoscopically or robotically apply a suture in a pursestring fashion and tie a knot during surgery. Embodiments of the present invention also facilitate the ICA by using a device that applies a pursestring suture to one side of a divided bowel wall and a closed staple line to the other side, optionally at the same time, e.g., simultaneously in response to a single actuation by the surgeon. Conventional methods do not provide a viable way to place a pursestring suture on a bowel other than laparoscopic or robotic intracorporeal suturing which is a highly skilled and time consuming maneuver.

According to certain embodiments, natural orifice transrectal specimen extraction is facilitated with the use of a self-expandable rectal retractor designed for safe insertion and removal, which inhibits damage or seeding of bowel contents to the rectal wall during the extraction process. Embodiments of the methods disclosed herein also enable intracorporeal placement of the anvil of a circular stapler by way of the rectal lumen as a natural orifice. According to particular embodiments, methods and devices disclosed herein result in resection, specimen extraction and creation of an ICA with the elimination of any abdominal incision other than those required for the laparoscopic or robotic ports, wherein all steps of the resection and anastomosis are performed intracorporeally.

As used herein, "resection" refers to the surgical removal or excision of a structure, or a segment of a structure, such as a segment of tubular tissue, e.g., a segment of colon and/or rectum. For example, methods described herein relate to the removal or excision of a diseased or defective segment of intestine or bowel (e.g., a diseased or defective segment of colon and/or rectum).

As used herein, "specimen" refers to a structure, or a segment of a structure, that is surgically removed or intended to be surgically removed. For example, surgical methods described herein may include the removal of a diseased or defective segment of intestine or bowel (e.g., a diseased or defective segment of colon and/or rectum), wherein the diseased or defective segment is also referred to as a specimen. As used herein, intestine, bowel, colon and rectum are non-limiting examples of "tubular tissue" having a lumen. In some cases, the specimen may be considered diseased and/or defective due to a disease or condition affecting the specimen, such as cancer, polyps, diverticulitis, Crohn's Disease, ulcerative colitis, endometriosis, ischemic colitis, rectal prolapse, tumors, etc.

As used herein, surgical steps that are performed "intra-corporeally" refer to steps that occur inside the body cavity, whereas surgical steps that are performed "extracorporeally" refer to steps that occur outside the body cavity.

As used herein, "suture" refers to a length of flexible material, such as a flexible strand or thread of material suitable for use in surgical procedures (e.g., thread material). The suture may be a pursestring suture that is placed around the edge of an open lumen in a bowel wall and fastened to the bowel using a plurality of fasteners (e.g., suture staples or suture clips) so that when the suture is drawn tight, the bowel opening is closed. The suture material may be strong enough to hold tissue securely and flexible enough to be knotted. A suture may be made from numerous materials known in the art.

Figure 12:
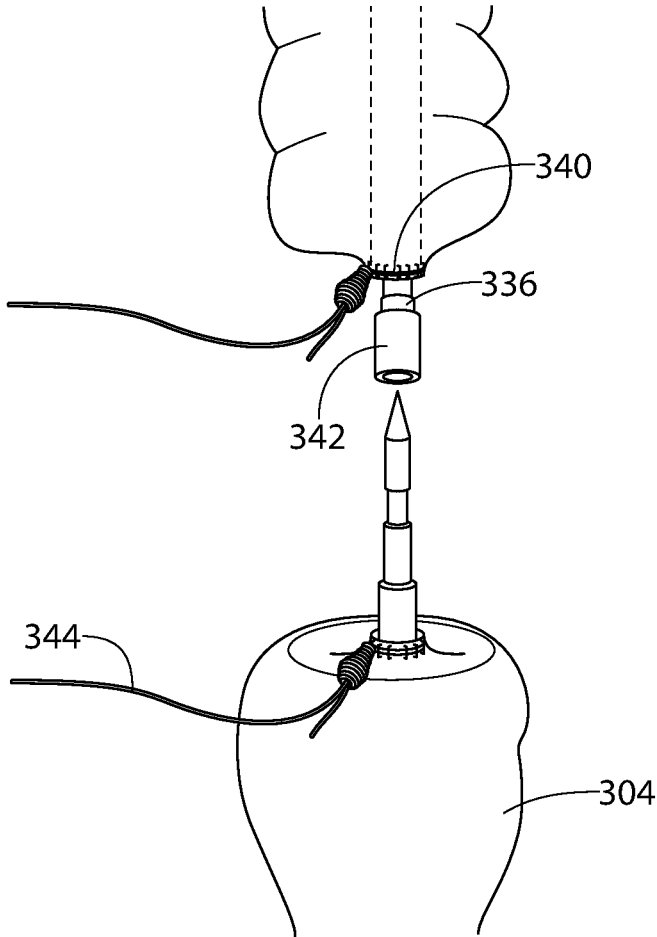
FIG. 12 is an illustration of an exemplary use of a trocar of a circular stapler in accordance with an exemplary embodiment of the present invention.

As used herein, a pre-formed adjustable fastening refers to the joining of at least two regions of the suture together by a fastening mechanism wherein a loop of suture extends from the fastening mechanism (the loop being configured to encircle a tubular tissue), and the fastening mechanism can be adjusted to tighten the loop of suture around the tubular tissue by decreasing the length or diameter of the loop (e.g., to tighten the loop around a bowel in order to close the bowel lumen around a trocar or anvil shaft extending from the bowel when performing an anastomosis, as shown in FIG. 12). Stated another way, the suture loop is tightened around the tubular tissue in order to draw the tissue edges together (e.g., in pursestring fashion). Although the terms "encircle" and "diameter" are used in reference to a loop formed by the suture, the loop is not necessarily circular but may be any shape that allows for the loop to be placed around a tubular tissue (e.g., substantially circular, substantially ovular, sub-stantially teardrop shaped, etc.). According to an embodi-ment (e.g., illustrated in FIGS. 2-4) the pre-formed adjust-able fastening may comprise a pre-formed adjustable knot, in which two regions of the suture are joined together by the knot, and a surgeon may adjust the knot to tighten a loop of the suture around a bowel wall. It is alternatively contem-plated that a pre-formed adjustable fastening may be knot-less; for example, two regions of a suture may be joined together by a connector, such as a ring or a self-locking clip that can be adjusted to tighten a loop of suture extending from the connector. A surgeon may tighten the suture loop around a tubular tissue according to any suitable method (e.g., any suitable method known in the art for tightening a pursestring suture). For example, a surgeon may pull one or more end portions of the suture extending from the pre-formed adjustable fastening, and/or push the pre-formed adjustable fastening forward while pulling or holding one or more end portions taught, and/or hold one or more of the end portions taught while allowing the pre-formed adjustable fastening to slide along the suture, thereby tightening the loop around the tubular tissue.

As used herein, "ports" are used interchangeably with "port incisions" and refer to incisions that are configured for the placement of laparoscopic and/or robotic instruments into a body cavity. Port incisions do not include incisions through which a segment of intestine (e.g., a segment of colon and/or rectum) is extracorporealized outside the body cavity during surgery, and therefore do not include incisions through which a segment of intestine (e.g., a resected bowel segment) is extracted out of a subject's body.

Laparoscopic and robotic surgery, typically referred to as minimally invasive surgery (MIS), are approaches in which the procedure is performed with a camera and instruments placed through small port incisions that may range from approximately 5 mm to approximately 12 mm, which facili-tate visualization and surgical maneuvers inside the body cavity (intracorporeally). Certain conventional types of lapa-roscopic and robotic surgery involving resection and anas-tomosis include steps that are both intracorporeal and extra-corporeal; for example, the laparoscopic or robotic portion of a surgery may be paused so that a segment of intestine can be extracorporealized outside the body through an additional incision that is not a port incision (or an existing port incision can be extended to create a large incision), and those steps of the surgery (e.g., steps of resection and/or anasto-mosis) are then performed extracorporeally. According to particular embodiments of the present invention, all steps of resection and anastomosis are performed intracorporeally, with no steps of resection or anastomosis performed extra-corporeally.

According to one embodiment, performing colorectal MIS includes placement of a various number of ports but most commonly 4 or 5 ports through the abdominal wall for minimally invasive instruments and camera. For example, laparoscopic surgery may include placement of approxi-mately 5-approximately 12 mm diameter ports, depending on the size of the camera and instruments. According to an embodiment, the da Vinci Xi robotic platform utilizes three 8 mm diameter ports for the camera and robotic instruments, a 12 mm diameter port for a stapling device, and an accessory port of 5 mm diameter for the bedside assistant. Whether laparoscopic or robotic, the cumulative length/diameter of all port incisions may be approximately 40 mm. Due to the small size and minimal abdominal wall trauma, these ports alone result in minimal abdominal wall trauma, post-operative pain and very low risk of port-site hernias. As used herein, the length, diameter or size of an incision refers to the longest dimension (e.g., length or width) of the port and the skin incisions may be longer by approximately 2 mm.

Each port incision may be approximately 15 mm in length or less, or approximately 12 mm or less, or approximately 10 mm or less. For example, one port incision may be approxi-mately 5 mm in size, another is approximately 12 mm in size to allow for placement of a robotic stapler and three other ports are approximately 8 mm in size. According to an embodiment, between 3-6 port incisions are made, e.g., 5 port incisions. The combined length of all the port incisions may be approximately 45 mm or less, or approximately 40 mm or less, or approximately 35 mm or less.

The present invention may provide a method of treating a disease or condition affecting a subject's bowel comprising using one or more of the embodiments of the surgical methods and/or devices described herein. For example, surgical methods and devices of the present invention may be used to treat benign conditions. Alternatively, surgical methods and devices of the present invention may be used to treat malignant conditions. Non-limiting examples of diseases or conditions that may be treated using embodi-ments of the surgical methods and/or devices described herein include cancer (e.g., bowel cancer, such as colon cancer or rectal cancer), polyps, diverticulitis, Crohn's Dis-ease, ulcerative colitis, endometriosis, ischemic colitis and rectal prolapse.

According to particular embodiments, the surgical meth-ods of the present invention are performed laparoscopically. According to additional embodiments, the surgical methods of the present invention are performed robotically. As described herein, embodiments of the method do not include making any abdominal wall incisions, except for port incisions, as the steps of resecting the specimen, removing the specimen through the rectum, and performing an anastomosis are performed intracorporeally, without any steps performed extracorporeally.

Referring to FIGS. 1-13, embodiments of the methods described herein include removing a specimen 300 (e.g., a diseased or defective segment of intestine, such as a diseased or defective segment of colon and/or rectum) from an intestine or tubular tissue 107, having a central lumen 105, preserving the normal, non-diseased, or "healthy" portions of the intestine that are not intended for removal, and performing an anastomosis to restore intestinal continuity. Normal portions of the bowel or tubular tissue 107 that are not removed are referred to as the proximal bowel portion 302 and distal bowel portion 304. Following resection of the specimen 300, the proximal bowel portion 302 and the distal bowel portion 304 may be joined together to form anastomosis 322, so that there is continuity between the proximal interior lumen 306 of the proximal bowel portion 302 and the distal interior lumen 308 of the distal bowel portion 304.

According to one embodiment, a method of intracorporeally resecting the specimen 300 from a subject (e.g., a diseased or defective bowel segment, such as a diseased or defective segment of colon and/or rectum) comprises intracorporeally resecting the specimen 300; extracting the specimen 300 through the subject's rectum; and intracorporeally forming anastomosis 322 between the proximal bowel portion 302 and the distal bowel portion 304. Resecting the specimen 300 may comprise separating the specimen 300 from the bowel by dividing the bowel wall 212 at a proximal margin of resection 312 (e.g., transversely across the lumen), thereby separating the specimen 300 from the proximal bowel portion 302; and dividing the bowel wall 212 at a distal margin of resection 314 (e.g., transversely across the lumen), thereby separating the specimen 300 from the distal bowel portion 304. Dividing the bowel wall 212 at the proximal margin of resection 312 and distal margin of resection 314 may be performed in any order, e.g., the bowel wall 212 may be divided at the proximal margin of resection 312 and subsequently divided at the distal margin of resection 314, or the bowel wall 212 may be divided at the distal margin of resection 314 and subsequently divided at the proximal margin of resection 312.

Referring to FIGS. 1-13, the method may comprise separating the specimen 300 from the proximal bowel portion 302 by dividing the bowel wall 212 at the proximal margin of resection 312 (e.g., transversely across the lumen), thereby separating the specimen 300 from the proximal bowel portion 302; optionally closing the proximal interior lumen 324 of the specimen 300 by applying staples 114 to the proximal edge portion 310 of the specimen 300, and placing a suture 118 around the edge portion 316 of the proximal bowel portion 302 (an edge portion being adjacent to the open lumen). The steps of (1) dividing the bowel wall 212 at a proximal margin of resection 312, thereby separating the specimen 300 from the proximal bowel portion 302, (2) closing the proximal interior lumen 324 of the specimen 300 by applying staples 114 to the proximal edge portion 310 of the specimen 300, and (3) placing suture 118 around an edge portion 316 of the proximal bowel portion 302 may be performed simultaneously, or substantially simultaneously.

According to an embodiment illustrated in, for example FIGS. 1-6, the method comprises separating the specimen 300 from the distal bowel portion 304 by dividing the bowel wall 212 at a distal margin of resection 314 (e.g., transversely across the lumen), thereby separating the specimen 300 from the distal bowel portion 304; optionally closing a distal interior lumen 326 of the specimen 300 by applying staples 114 to the distal edge portion 318 of the specimen 300; and placing suture 118 around the edge portion 320 of the distal bowel portion 304 adjacent to the distal interior lumen 308. The steps of (1) dividing the bowel wall 212 at a distal margin of resection 314, thereby separating the specimen 300 from the distal bowel portion 304, (2) closing the distal interior lumen 308 of the specimen 300 by applying staples 114 to the distal edge portion 318 of the specimen, and (3) placing suture 118 around the edge portion 320 of the distal bowel portion 304 may be performed simultaneously, or substantially simultaneously.

According to particular embodiments, the surgical instrument 102 is configured to apply the staples 114 and suture 118 simultaneously (e.g., in a single motion), upon actuation by a surgeon. The surgical instrument 102, as disclosed in further detail below, may comprise a cutting mechanism 176, stapling mechanism 174, and suturing mechanism 172 that simultaneously, or substantially simultaneously, divide the bowel wall at the distal margin of resection 314, close the distal interior lumen 326 of the specimen 300 by applying staples 114 to the distal edge portion 318 of the specimen 300, and place suture 118 around the edge portion 320 of the distal bowel portion 304. According to particular embodiments, the suturing mechanism of 172 the surgical instrument 102 includes a suture having a pre-formed adjustable fastening (e.g., a pre-formed knot, such as a pre-formed slipknot).

Referring to FIGS. 6-9, after the specimen 300 has been separated from the normal or "healthy" bowel, and optionally stapled at its proximal edge portion 310 and distal edge portion 318 to close its proximal interior lumen 324 and distal interior lumen 326, the method may further comprise extracting the specimen 300 through the subject's rectum. According to particular embodiments, extracting the specimen 300 through the subject's rectum comprises transanally inserting a grasping tool 210 through the distal bowel portion 304, grasping the specimen 300 with the grasping tool 210, and extracting the specimen 300 through the subject's rectum. According to an embodiment, the method comprises transanally inserting a transrectal retractor 328 through the distal bowel portion 304, and subsequently inserting the grasping tool 210 through the transrectal retractor 328.

In an embodiment, the self-expandable transrectal retractor 328 is used to transrectally remove the specimen 300 (e.g., a resected bowel segment). The transrectal retractor 328 may be used in accordance with embodiments of the surgical methods described herein. The transrectal retractor 328 may be configured to be positioned inside a subject's rectum and expand the bowel wall substantially uniformly (i.e., increase the rectal lumen's circumference), prevent or reduce tearing or other trauma to the bowel wall upon insertion of a grasping device 210 through the rectum, and prevent or reduce contamination as the specimen 300 is removed through the rectum.

According to an embodiment, a transrectal retractor 328 comprises a substantially cylindrical body comprising a deformable material extending along a longitudinal axis. The substantially cylindrical body has an exterior, an interior passage 202, and a top edge portion 204 defining an opening into the interior passage. The top edge portion 204 is configured to expand around an opening to the bowel's lumen that has been exposed by dividing the bowel wall, e.g., at the distal margin of resection 314. According to an embodiment, a drawstring 206 extends through the interior passage 202 and is coupled to the top edge portion 204. When the transrectal retractor 328 is positioned in the subject's bowel lumen, the substantially cylindrical body extends longitudinally along a distance of the bowel lumen, e.g., from the exposed opening in the bowel lumen to the anal orifice or beyond the anal orifice, with the exterior of the substantially cylindrical body in contact with the bowel's interior wall. By self-expanding, the transrectal retractor 328 expands the bowel lumen along that distance and protects the lumen so that a grasping instrument 210 can be safely inserted transanally through the interior passage 202 to grasp the specimen 300, and the specimen 300 can be safely removed transanally without coming into contact with the bowel lumen. According to particular embodiments, the substantially cylindrical body comprises a bottom edge portion (not shown) at the end that is opposite to the top edge portion, which also defines an opening to the interior passage 202. The bottom edge portion may be configured to remain outside of the anal orifice.

According to an embodiment, the transrectal retractor 328 is detachably coupled to an insertion instrument that is insertable through the rectum, e.g., the insertion instrument may be a conventional surgical instrument, such as a circular stapler or the like. The insertion instrument may be slidably removed from the transrectal retractor 328 (and removed transanally from the rectum) after the transrectal retractor 328 is placed in the rectum. The method may further comprise transanally inserting a grasping tool 210 and optionally an endoscopic bag or endocatch through the transrectal retractor 328, grasping the specimen 300, optionally placing the specimen 300 in a transrectally inserted endobag, and transanally extracting the specimen 300 through the interior of the transrectal retractor 328. The method may further comprise removing the transrectal retractor 328 by pulling the drawstring 206, thereby pulling the substantially cylindrical body out of the rectum.

According to an embodiment, the insertion instrument comprises an external sheath 208 that is slidably coupled to and surrounding at least a portion of the exterior of the substantially cylindrical body. The material of the substantially cylindrical body is self-expandable (e.g., biased to expand outward when the external sheath is removed). The substantially cylindrical body thus is configured to expand outward and increase the circumference of its internal passage, thereby expanding the rectum's luminal circumference, e.g., as an external sheath 208 is slidably moved away from the top edge portion 204 in a longitudinal direction.

According to an embodiment, the transrectal retractor 328 is removably coupled to a circular stapler 330 (e.g. FIG. 10) comprising a stapling cartridge and an anvil 336 component removably coupled thereto. The top edge portion 204 may include a rim comprising a plurality of notches or an expandable ring-like structure configured to removably secure the transrectal retractor 328 to the circular stapler.

According to an embodiment, a method of using the transrectal retractor 328 to intracorporeally resect the specimen 300 from the subject comprises transanally inserting the transrectal retractor 328 through a distal bowel portion 304 (e.g., after the bowel has been divided at a distal margin of resection 314 to expose an opening to the lumen), and positioning the transrectal retractor 328 within the bowel's lumen so that the top edge portion 204 of the transrectal retractor 328 surrounds the opening to the lumen 308 in the distal bowel portion 304.

14

Figure 9:
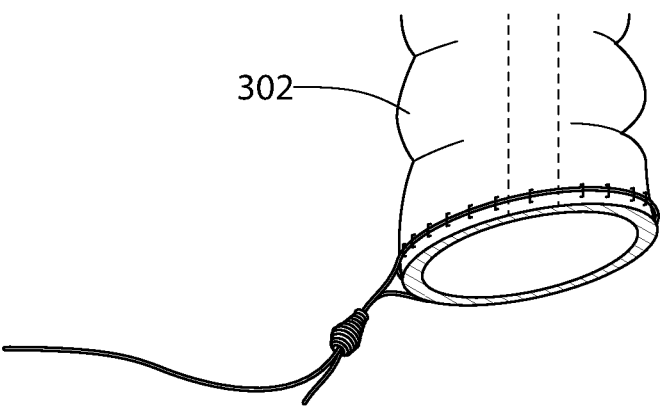
FIG. 9 is an illustration of an exemplary use of a rectal extractor in accordance with an exemplary embodiment of the present invention.
Figure 9:
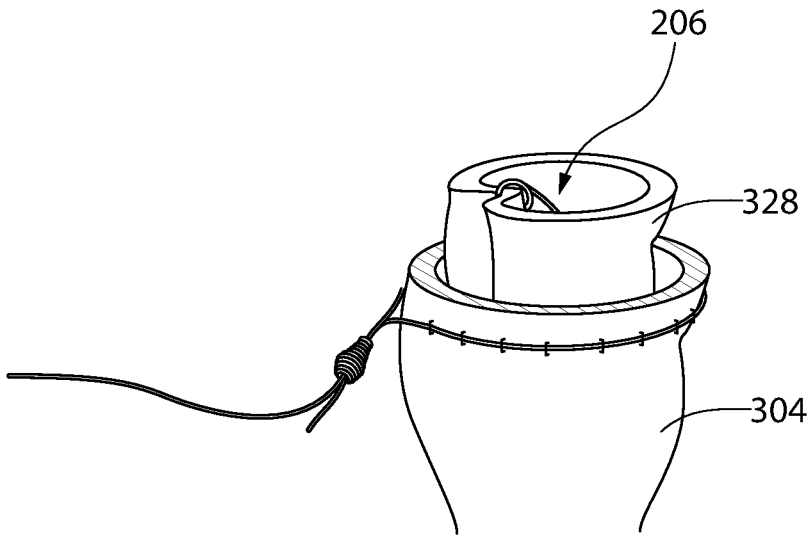
Figure 10:
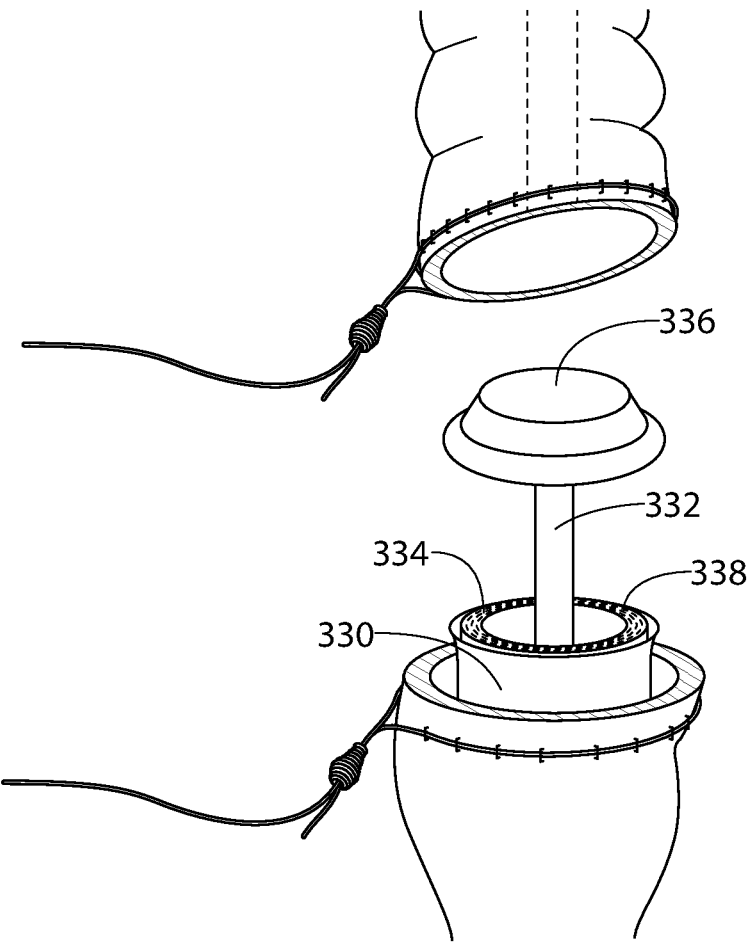
FIG. 10 is an illustration of an exemplary circular stapler in accordance with an exemplary embodiment of the present invention.

Referring to FIGS. 9-10, after the specimen 300 has been extracted from the subject, the method may further comprise intracorporeally forming an anastomosis 322 between the proximal bowel portion 302 and the distal bowel portion 304. Intracorporeally forming the anastomosis 322 may be performed with the use of circular stapler 330. Various circular staplers are known in the art and may be suitable for use in accordance with the present invention. According to particular embodiments, circular stapler 330 includes an elongated shaft that has actuating and adjustment mechanisms utilized by the surgeon, and a stapling mechanism 334 mounted to the elongated shaft. The stapling mechanism 334 includes a stapling cartridge 338, also referred to as a head unit, which contains a plurality of staples that may be configured in a substantially concentric circular array. A substantially circular or ovular cutting knife may be concentrically mounted in the cartridge interior to the staples for axial travel therein. Extending axially from the center of the cartridge is a movable trocar shaft 332 that is adapted to have an anvil component 336 removably coupled thereto. The anvil component 336 is configured to form the ends of the staples as they are driven into it. The distance between a distal face of the staple cartridge 338 and the anvil 336 component is commonly controlled by an adjustment mechanism that is mounted to the stapler shaft for controlling the axial movement of the trocar 332. Tissue that is clamped between the staple cartridge 338 and the anvil 336 is stapled and cut when the actuating mechanism is activated by the surgeon, thereby excising the suture staples and staples so that they can be removed from the subject.

Figure 11:
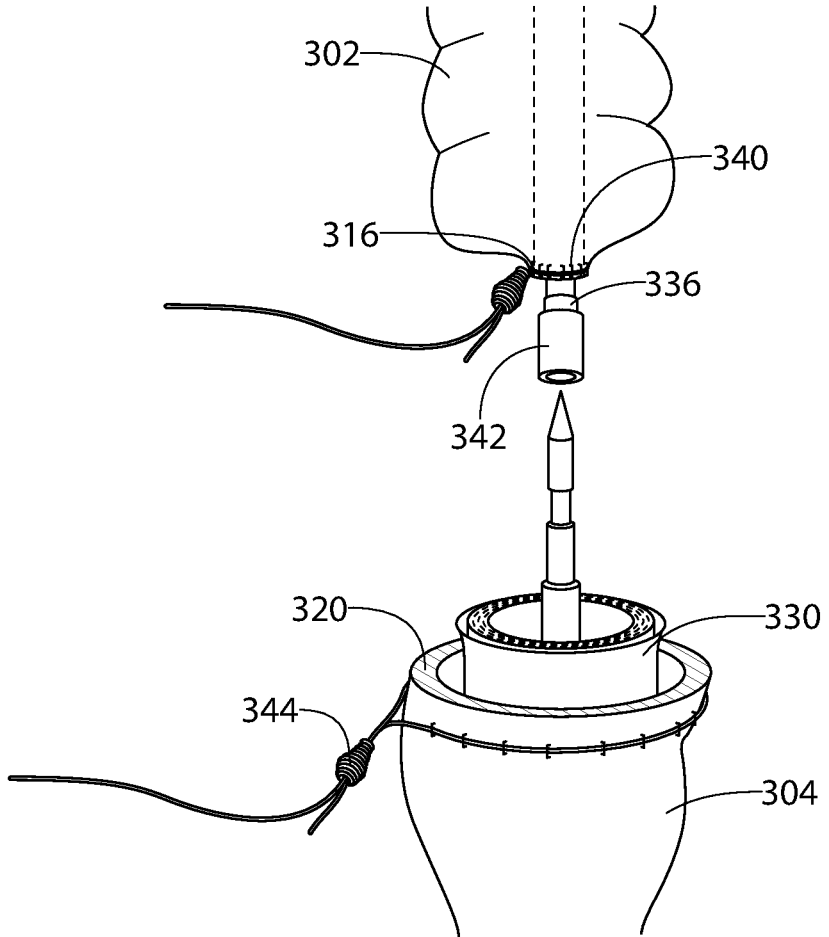
FIG. 11 is an illustration of an exemplary use of an anvil and circular stapler in accordance with an exemplary embodiment of the present invention.
Figure 13:
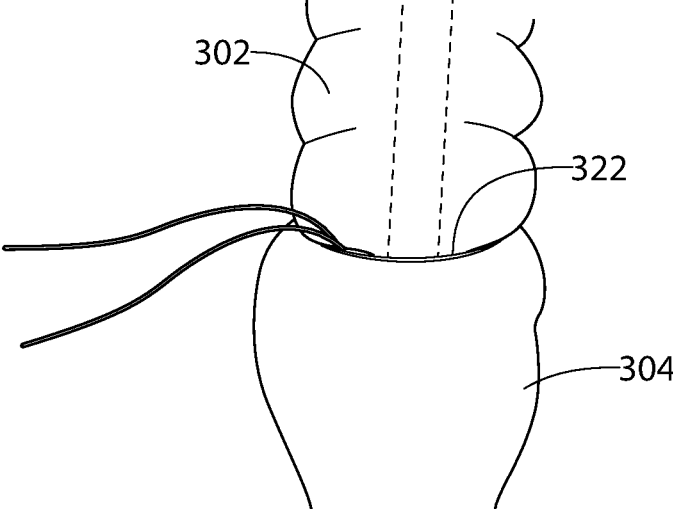
FIG. 13 is an illustration of an exemplary anastomosis in accordance with an exemplary embodiment of the present invention.
Figures 14A, 14B, 14C:
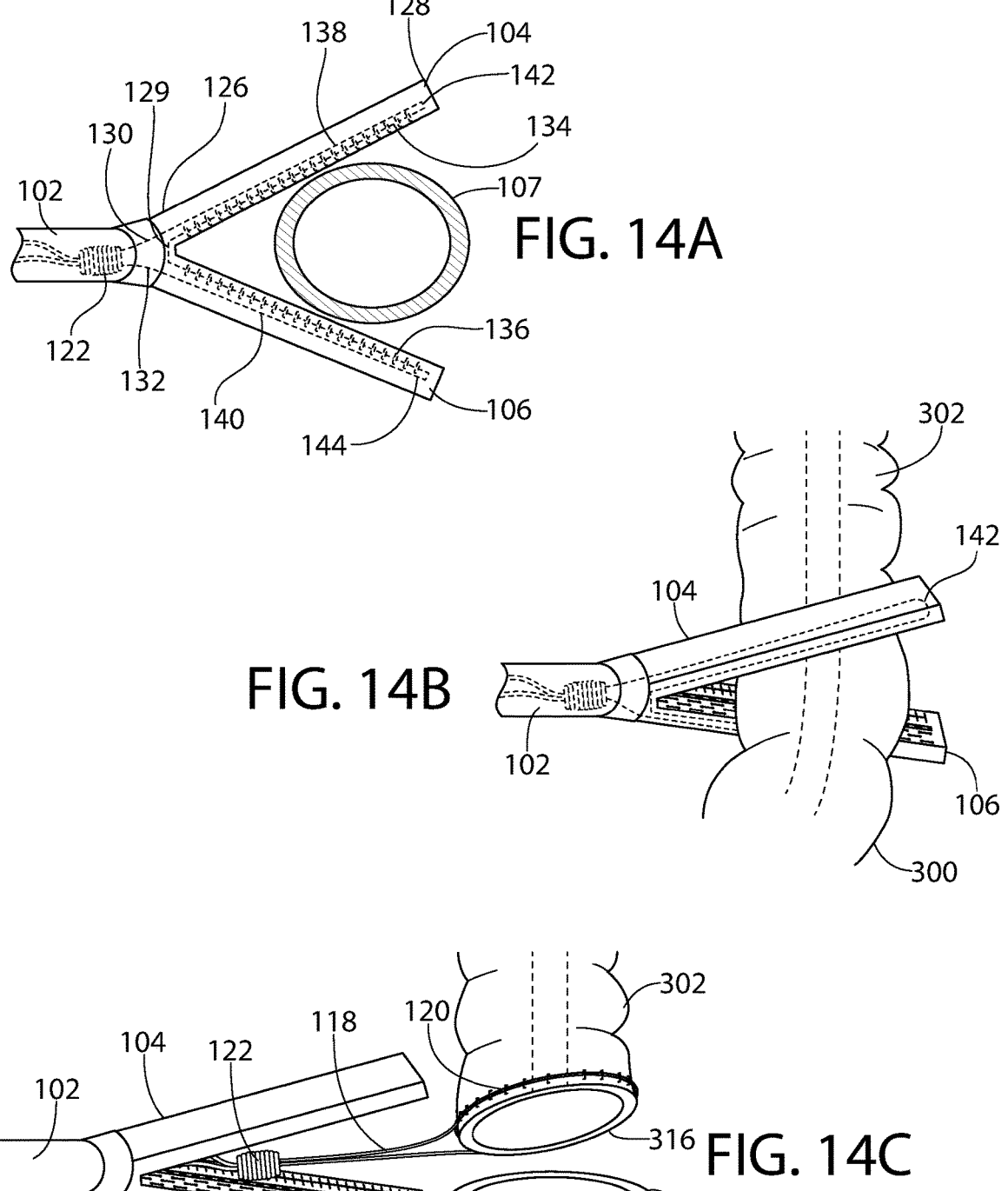
FIG. 14A-C is an illustration of an embodiment of an exemplary surgical device in accordance with an exemplary embodiment of the present invention.
Figure 15A:
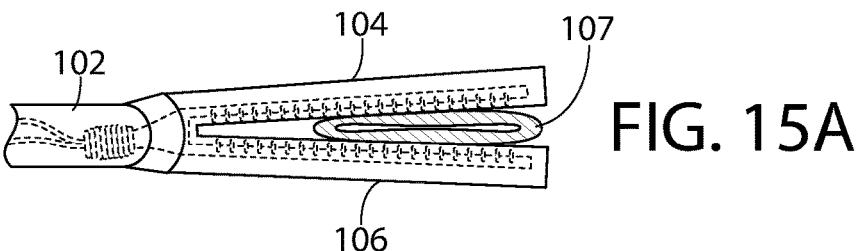
FIG. 15A-C is an illustration of an exemplary surgical device in accordance with an exemplary embodiment of the present invention.
Figure 15B:
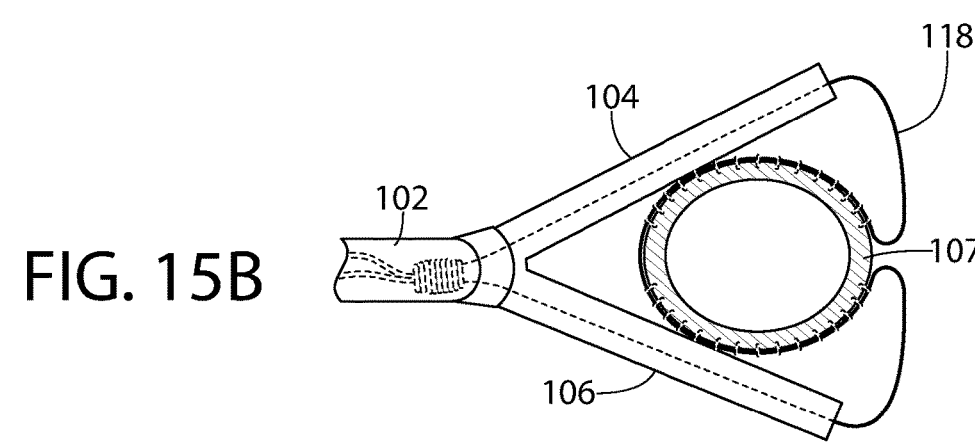
Figure 15C:
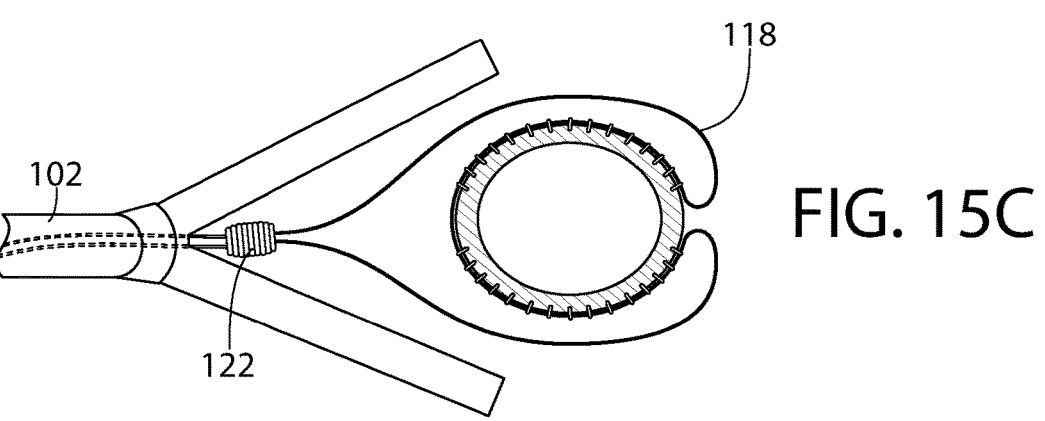
Figure 16A:
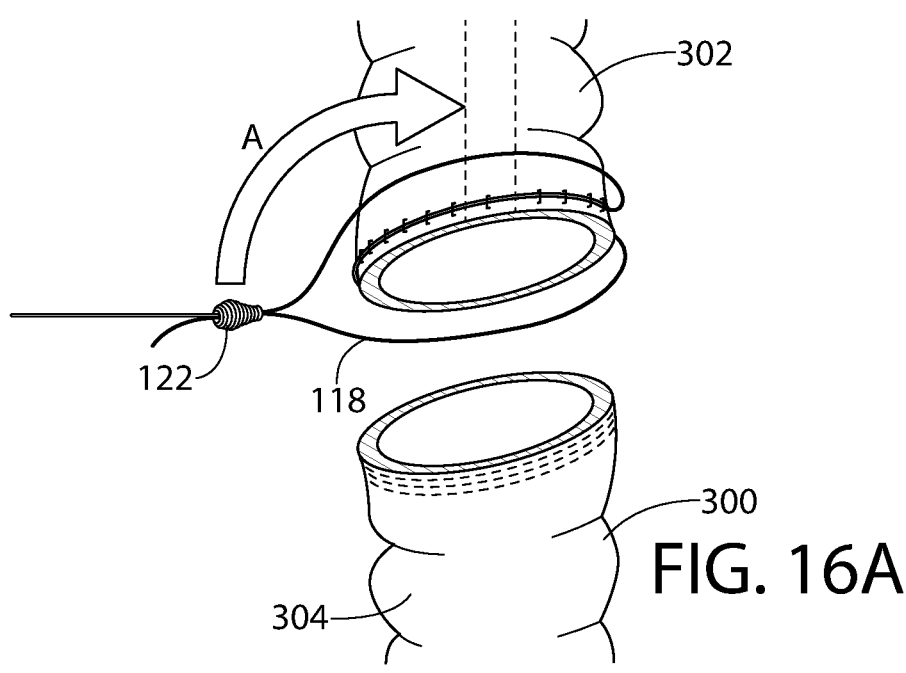
FIG. 16A-B is an illustration of a suture being applied around a bowel wall by an exemplary surgical device in accordance with an exemplary embodiment of the present invention.
Figure 16B:
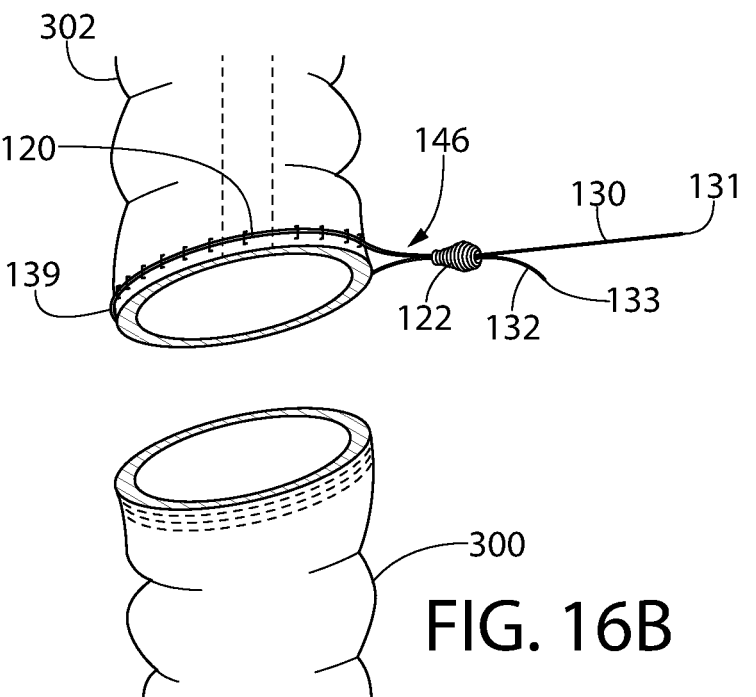
Figure 17:
FIG. 17 is a top view of an exemplary surgical device in accordance with an exemplary embodiment of the present invention.
Figure 17:
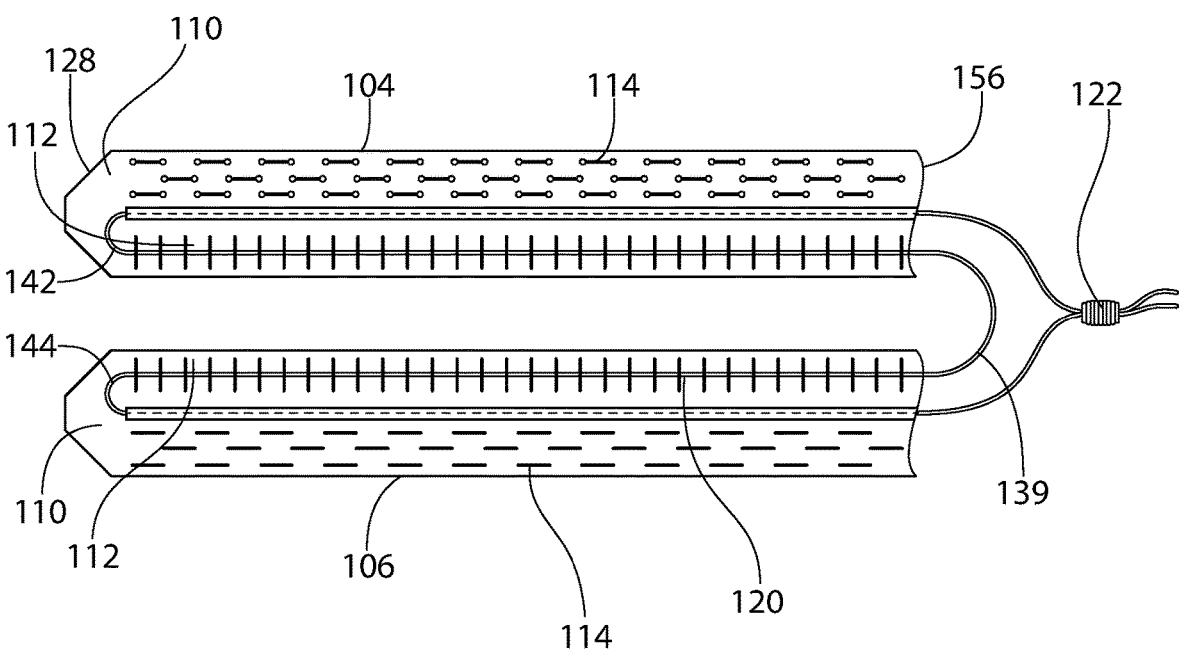
Figure 18:
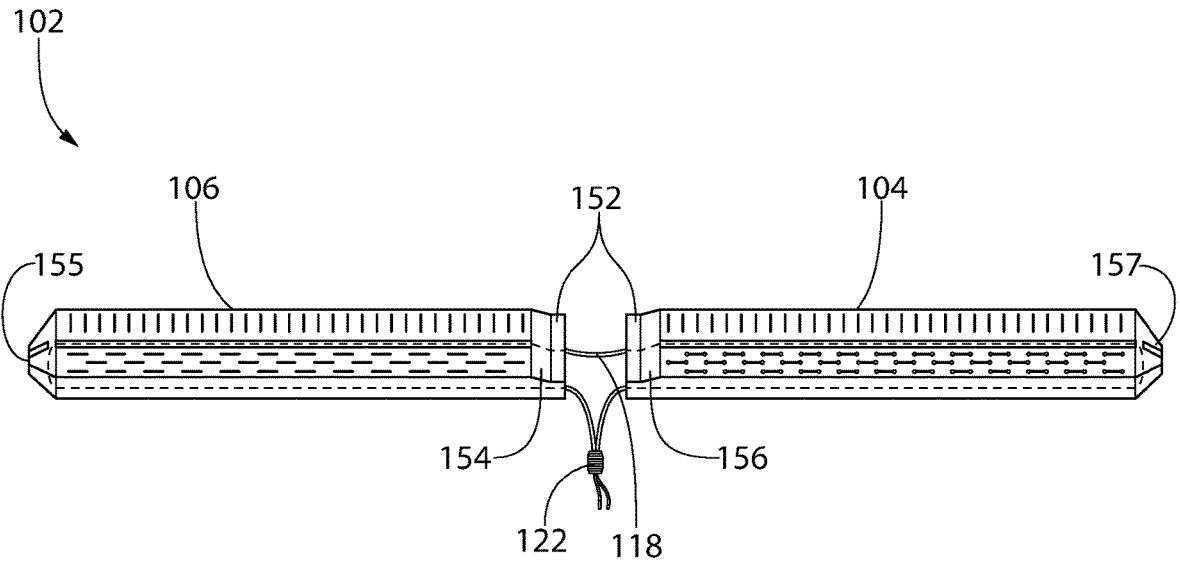
FIG. 18 is an illustration of a first arm and second arm of an exemplary surgical device in accordance with an exemplary embodiment of the present invention.

Referring to FIGS. 11-13, the method may further comprise detaching the anvil component 336 from the stapling cartridge 338, closing the edge portion 316 of the proximal bowel portion 302 around the anvil component 336, and closing the edge portion 320 of the distal bowel portion 304 around the stapling cartridge 330. Closing the edge portion 316 of the proximal bowel portion 302 around the anvil component 336 may comprise tightening the suture 340 around a shaft 342 extending axially from the anvil component 336; and closing the edge portion 320 of the distal bowel portion 302 around the stapling cartridge 330 comprises tightening the suture 344 around a shaft extending axially from the stapling cartridge 330. The anvil component 336 and stapling cartridge 330 are then coupled together, and the circular stapler is actuated to form the anastomosis 322 between the proximal bowel portion 302 and distal bowel portion 304, thereby providing continuity between the proximal interior lumen 306 of the proximal bowel portion 302 and the distal interior lumen 308 of the distal bowel portion 304. When the surgeon activates the stapler, the staples attach the two bowel ends together and a knife in the stapler (e.g., a substantially circular knife), which is concentrically mounted interior to the staples, divides the tissue surrounding the suture staples and suture, excising them, and the excised tissue comprising the suture staples and suture become disposed in a chamber of the stapler, which the surgeon removes.

According to an embodiment, a method of using the surgical device 102 to apply a suture 118 around a tubular tissue (e.g., laparoscopically or robotically) comprises inserting the surgical device into a body cavity through a port incision, clamping the tubular tissue between the first arm 104 and the second arm 106, actuating the cutting mechanism 176 to divide the tubular tissue, thereby creating an open lumen, and actuating the suturing mechanism 172 to attach the first and second rows of suture staples 120 to the tubular tissue adjacent to the open lumen, wherein the suture 118 comprising the pre-formed adjustable fastening 122 detaches from the surgical device 102 and forms a loop around the tubular tissue, with a portion of the suture 118 extending through the suture staples 120. As described herein, the suture 118 forms the loop upon or after detaching from the surgical device 102. For example, after the suture staples 120 attach to the tubular tissue, the suture 118 may automatically detach from or "fall out" of the surgical device 102 after the first arm 104 and second arm 106 are opened (e.g., when a surgeon pulls the device away from the bowel wall). As described herein, the steps of actuating the cutting mechanism 176 and actuating the suturing mechanism 172 may occur simultaneously or substantially simultaneously, e.g., in response to a single actuation by a surgeon. The method may further comprise tightening the suture 118 around the tubular tissue by pulling one or more of the first end portion 130 and the second end portion 132 of the suture 118, thereby sliding the pre-formed adjustable fastening 122 and closing the loop.

According to an embodiment, a method of using the surgical device 102 to intracorporeally resect a bowel specimen from a subject (e.g., laparoscopically or robotically) comprises inserting the surgical device into a body cavity through a port incision, clamping the first arm 104 and the second arm 106 over a proximal margin of resection between the specimen 300 and a healthy bowel portion, actuating the cutting mechanism 176 to divide the bowel at the proximal margin of resection 312, actuating the stapling mechanism 174 to close an interior lumen 324 of the specimen 300 by applying the staples 114 to a proximal edge portion 310 of the specimen 300, actuating the suturing mechanism 172 to attach the first and second rows of suture staples 120 to an edge portion 316 of the proximal bowel portion 302, wherein the suture 118 comprising a pre-formed adjustable fastening 120 detaches from the surgical device 120 and forms a loop around the edge portion 316 of the proximal bowel portion 302, a portion of the suture 118 extending through the suture staples 120; and clamping the first arm 104 and the second arm 106 over a distal margin of resection 314 between the specimen 300 and a healthy bowel portion, actuating the cutting mechanism 176 to divide the bowel at the distal margin of resection 314, actuating the stapling mechanism 174 to close an interior lumen 324 of the specimen 300 by applying the staples 114 to a distal edge portion of the specimen 300, and actuating the suturing mechanism 172 to attach the first and second rows of suture staples 120 to an edge portion 320 of the distal bowel portion 304, wherein the suture 118 comprising the pre-formed adjustable fastening 122 detaches from the surgical device 102 and forms a loop around the edge portion 320 of the distal bowel portion 304, a portion of the suture 118 extending through the suture staples 120. As described herein, actuating the cutting mechanism 176, actuating the stapling mechanism 174 and actuating the suturing mechanism 172 occur simultaneously, or substantially simultaneously, in response to a single actuation by a surgeon.

Referring to FIGS. 1 and 14-26, the surgical device 102 may be configured to apply the staples 114 and suture 118 simultaneously (e.g., in a single motion), upon actuation by a surgeon. The surgical instrument 102 may comprise a cutting mechanism 176, a stapling mechanism 174, and a suturing mechanism 172 that simultaneously, or substantially simultaneously, divide the bowel wall 212 at the proximal margin of resection 312, close the proximal interior lumen 324 of the specimen 300 by applying staples 114 to the proximal edge portion 310 of the specimen, and place suture 118 around the edge portion 316 of the proximal bowel portion 302. According to particular embodiments, the suturing mechanism 172 of the surgical instrument 102 includes a suture having a pre-formed adjustable fastening 122 (e.g., a pre-formed knot, such as a pre-formed slipknot).

The surgical device 102 may comprise a suturing mechanism 172 for placing a suture around a tubular tissue (e.g., a bowel, such as colon or rectum). According to particular embodiments, a length of suture comprising a pre-formed adjustable fastening (e.g., a pre-formed knot, such as a pre-formed slipknot) is detachably coupled to the surgical device. According to an embodiment, the suture is a pursestring suture. By including a pre-formed adjustable fastening as part of the suture, a surgeon does not need to tie a knot in the suture after the suture is placed around the tubular tissue (e.g., around a bowel wall). According to particular embodiments, the length of suture comprising the pre-formed adjustable fastening is held in the instrument in a "folded" or bent position, and upon detaching from the instrument, the suture "unfolds" into a loop that surrounds the bowel or other tubular tissue (the loop extending from the pre-formed adjustable fastening). Thus, after the suture is positioned around the tubular tissue, a surgeon can tighten the suture, for example, by pulling on an end portion of the suture that extends from the pre-formed adjustable fastening (e.g., pre-formed knot). As described herein, the surgical device may include a cutting mechanism 176 and/or a stapling mechanism 174, in addition to the suturing mechanism 172.

According to an embodiment of the present invention, the surgical device 102 is connected to an actuating mechanism (not shown) (e.g., mechanically, and/or electrically, and/or remotely via computer, etc.), which means that the actuating mechanism is in communication with the surgical device 102 so that it can actuate the surgical device 102, e.g., via mechanical and/or electrical and/or remote means. The surgical device 102 and actuating mechanism may form part of a surgical system, such as a laparoscopic and/or robotic surgical system. The actuating mechanism is used by the surgeon to control and actuate the surgical device; for example, a surgeon may actuate the surgical device 102 with a single motion by pressing a button, or pulling a trigger, etc. During a surgical procedure, the surgical device 102 may be placed inside the subject's body cavity (e.g., through a port incision or natural orifice) while the actuating mechanism remains outside the body cavity and is controllable by the surgeon (e.g., the actuating mechanism may be part of the control center in a robotic system that allows the surgeon to view the surgical field and control movement of the endoscopic instruments). For example, as illustrated in FIG. 1, the surgical device 102 may be coupled to an arm 148 that forms part of a laparoscopic or robotic surgical system, such as a da Vinci surgical system. The actuating mechanism may comprise a handle portion that is grasped by the surgeon.

Referring to FIGS. 1 and 14-28, the surgical device 102 comprises a first arm 104 and a second arm 106 each having a longitudinal length with opposite proximal end portsion 154, 156 and distal end portions 155, 157. The first arm 104 and second arm 106 are movable between an open position (e.g., FIG. 14A) and a clamped position (e.g., FIG. 15A). At least one of the first arm 104 and the second arm 106 is/are movable between the open position and clamped position. The first arm 104 and the second arm 106 may be closed over a tubular tissue 107, e.g., over a bowel, in a clamped position. According to particular embodiments, the first arm 104 and second arm 106 have a hinge mechanism 152 that hinges them together at their proximal end portions 154, 156. The first arm 104 and the second arm 106 may be formed as a single integral unit that are coupled together at their proximal end portions 154, 156, or the first arm 104 and the second arm 106 may be formed as separate units that are then coupled together. When the first arm 104 and second arm 106 are in the clamped position, the surgical device 102 may have small enough dimensions to fit through a port incision for placement in a body cavity. The total height of the first arm 104 and second arm 106 clamped together may be less than approximately 12 mm, between approximately 12 mm and approximately 15 mm, or greater than approximately 15 mm.

Referring to FIGS. 14-24, the surgical device 102 may include a suturing mechanism 172, which comprises a length of suture 118 (e.g., a pursestring suture) that extends through suture staples 120. According to an embodiment, a first row of suture staples 120 is positioned along the longitudinal length in the first arm 104, and a second row of suture staples 120 is positioned along the longitudinal length in the second arm 104, as illustrated, e.g., in FIG. 17. The length of suture 118 comprises a first end region 130 and a second end region 132, which include opposite first and second ends, respectively. According to particular embodiments, the first and second end regions 130, 132 are coupled together by a pre-formed adjustable fastening 122 (e.g., a pre-formed knot, such as a pre-formed slipknot), a first threaded region 134 of the suture extends through the first row of suture staples 120 in the first arm 104, and a second threaded region 136 of the suture extends through the second row of suture staples 120 in the second arm 106. In an embodiment, the length of suture 118 further comprises a first unthreaded region 138 extending along the longitudinal length of the first arm 104, and a second unthreaded region 140 extending along the longitudinal length of the second arm 106. According to an embodiment, the first threaded region 134 and the first unthreaded region 138 of the suture are detachably coupled to the first arm 104, the second threaded region 136 and the second unthreaded region 140 of the suture are detachably coupled to the second arm 106, and the first end portion 130 and the second end portion 132 of the suture, which are coupled together by a knot, extend away from the first arm 104 and the second arm 106.

According to particular embodiments, the length of suture 118 is formed into a first bend 142 between the first unthreaded region 138 and the first threaded region 134, and a second bend 144 between the second threaded region 136 and the second unthreaded region 140. According to an embodiment, each of the first bend 142 and the second bend 144 is approximately 180 degrees so that the first unthreaded region 138 of suture 118 is substantially parallel to the first threaded region 134 of suture 118 in the first arm 104, and the second unthreaded region 140 of suture 118 is substantially parallel to the second threaded region 136 of suture 118 in the second arm 106.

The suture 118 is configured so that after detaching from the surgical device 102, it is biased to become unbent at the first bend 142 and the second bend 144 so that it forms a loop (e.g., a substantially circular or ovular loop) that extends from the pre-formed adjustable fastening. For example, the suture 118 may be held in the surgical device 102 in a "folded" position (i.e., folded at the first bend 142 and the second bend 144), and upon detaching from the surgical device 102, the suture 118 "unfolds" or straightens into a loop 146 that extends from the pre-formed adjustable fastening 122 and encircles or surrounds the bowel or other tubular tissue 107. As illustrated, for example, in FIGS. 16A and 16B, the end regions 130, 132 of suture comprising the pre-formed adjustable fastening 122 are moved to the opposite side of the bowel wall (as indicated by arrow "A" in FIG. 16A) after detaching from the first arm 104 and the second arm 106. For example, after detaching from the first arm 104 and the second arm 106 the suture 118 may unfold automatically so that it surrounds the bowel or other tubular tissue 107 (e.g., by swinging around the open lumen after detaching from the surgical device), or the suture 118 may be unfolded by a surgeon, e.g., by utilizing a surgical tool to grasp the suture 118 and place it around an edge portion of the tubular tissue 107 adjacent to the open lumen. According to an embodiment, the central bend 139 and threaded regions 134, 136 of the suture 118 remain substantially in place on the bowel wall after the suture staples 120 are applied to the bowel wall, while the unthreaded regions comprising the end portions 130, 132 and pre-formed adjustable fastening 122, are moved around the open lumen and so that when the suture loop surrounds the bowel wall the pre-formed adjustable fastening (e.g., knot) 122 is on the opposite side of the tubular tissue 107 from the central bend 139 disposed between the threaded regions 134, 136.

Referring to FIGS. 16A-18, the length of the suture 118 may comprise opposite first end 131, second end 133, first end region 130, and second end region 132. The first end region 130 of the suture 118 may extend from the first end 131 to the pre-formed adjustable fastening 122 and then to the proximal end portion 154 of the first arm 104, the first unthreaded region 138 of the suture 118 then extends from the proximal end portion 154 of the first arm 104 toward the distal end portion of the first arm 104, the suture 118 then forms a first bend 142 that is adjacent to the distal end 155 of the first arm 104, the first threaded region 134 of the suture 118 then extends through the first row of suture staples 120 toward the proximal end portion 154 of the first arm 104, the suture 118 then forms a central bend 139 that extends between the proximal end portions 154, 156 of the first arm 104 and the second arm 106, the second threaded region 136 of the suture 118 then extends through the second row of suture staples 120 toward the distal end 157 of the second arm 106, the suture 118 then forms into a second bend 144 that is adjacent to the distal end portion 157 of the second arm 106, the second unthreaded 140 region of the suture 118 then extends toward the proximal end portion 156 of the second arm 106, the second end region 132 then extends to the pre-formed adjustable fastening 122 and then to the second end 133.

Figure 21:
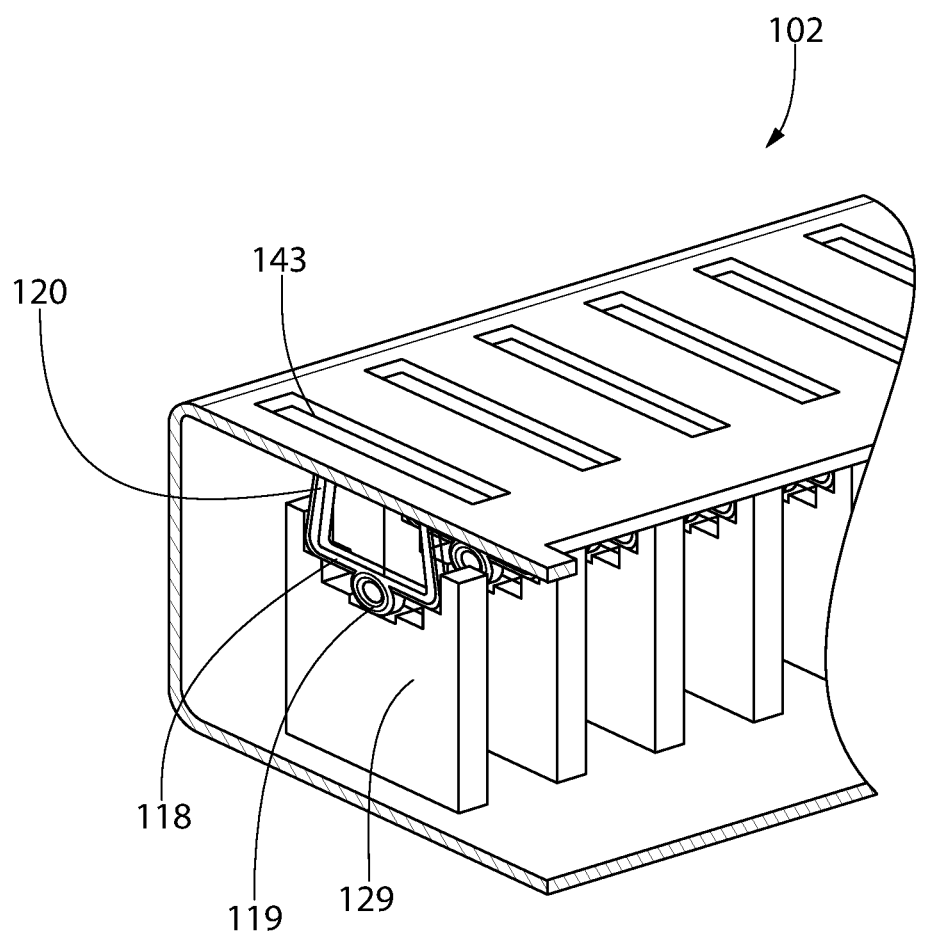
FIG. 21 is a cross-sectional side view of arm of an exemplary surgical device in accordance with an exemplary embodiment of the present invention.
Figure 22:
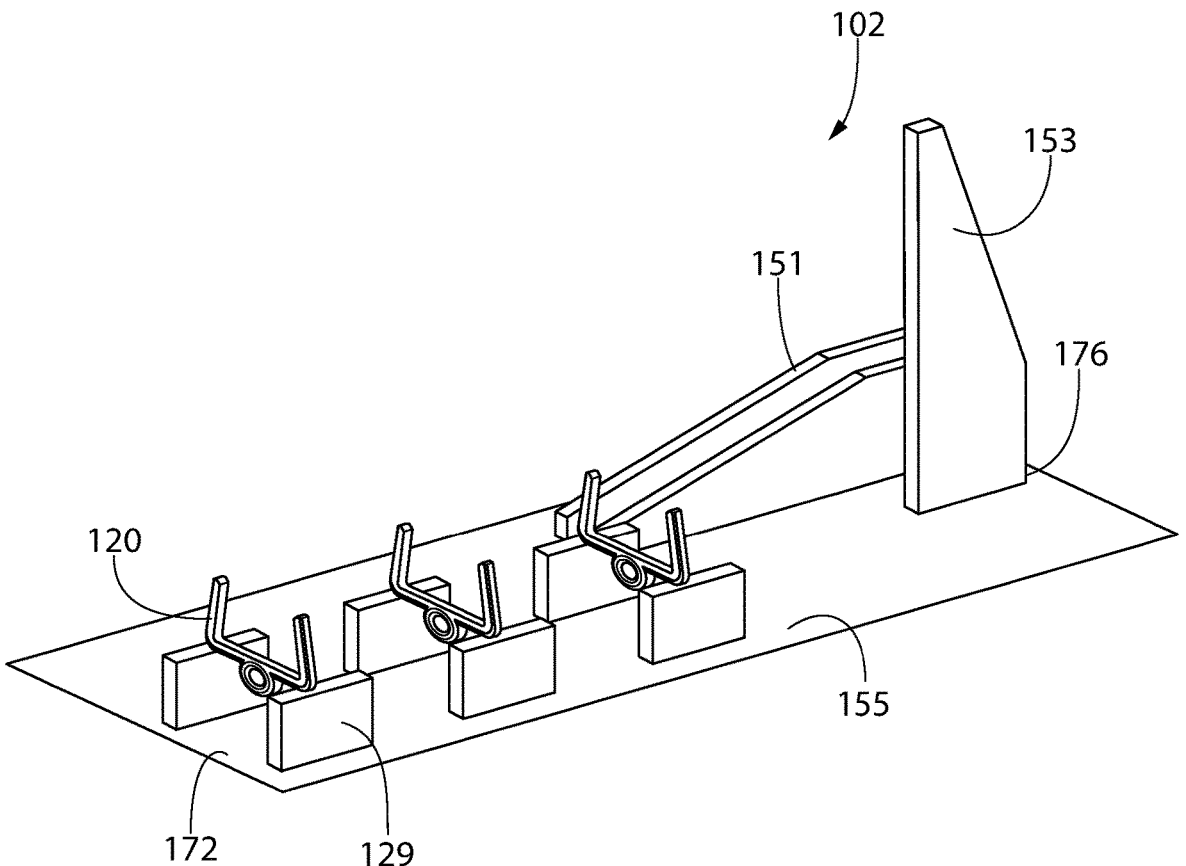
FIG. 22 is a partial view of an exemplary surgical device in accordance with an exemplary embodiment of the present invention.
Figure 23:
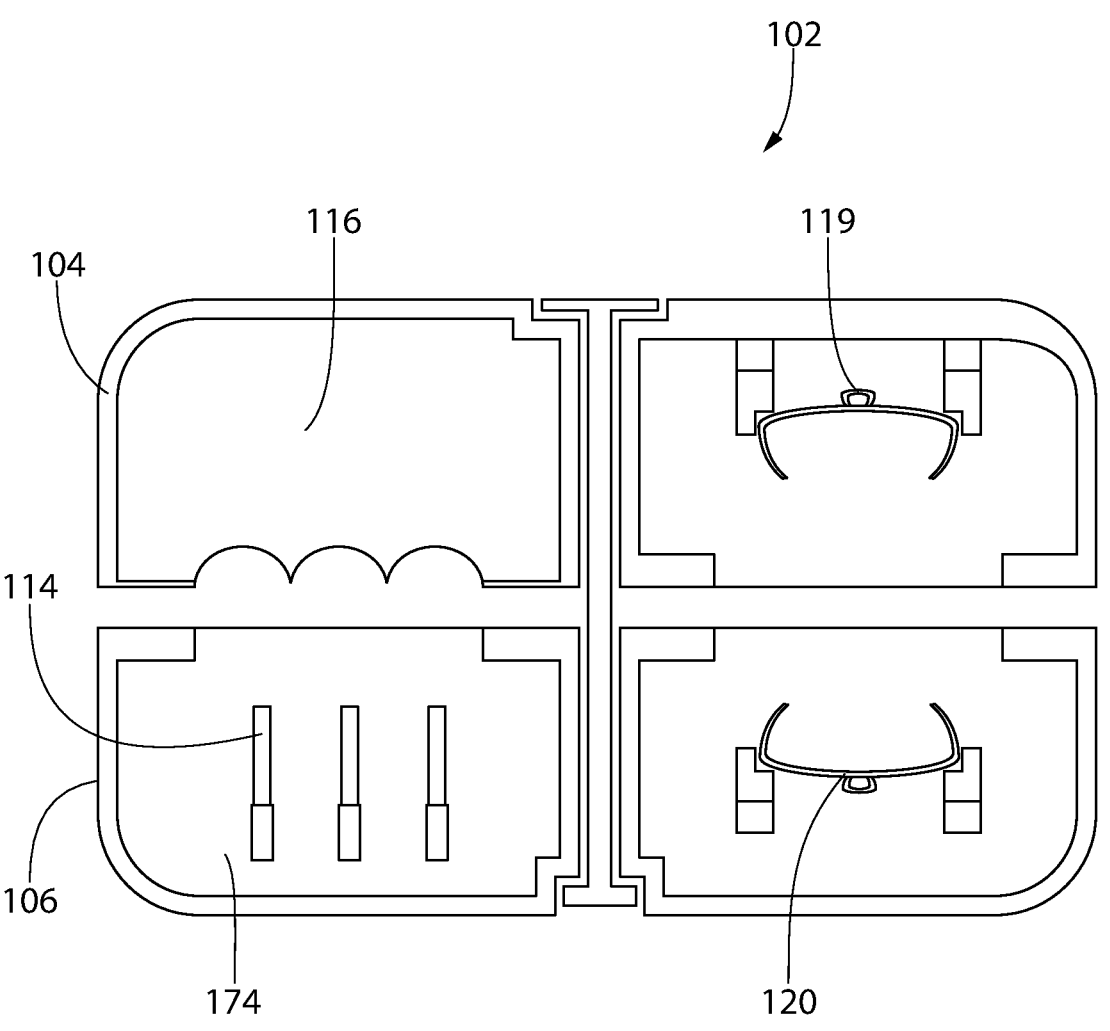
FIG. 23 is a cross-sectional side view of an exemplary surgical device in accordance with an exemplary embodiment of the present invention.

Referring to FIGS. 19-22, each suture staple 120 may include an opening 127, and the suture 118 extends through the openings 127. The suturing mechanism 172 of the surgical device 102 may comprise an interior portion 141 for housing the suture staples 120, and one or more slots 143 for permitting passage of the suture staples 120 out of the interior portion 141. The surgical device 102 may also comprise a pushing mechanism 129 configured to push the suture staples out of the interior portion 141 when the suturing mechanism 172 is actuated; for example, the pushing mechanism 129 may comprise one or more protrusions disposed underneath each suture staple. Different embodiments of the pushing mechanism 129 are illustrated in FIGS. 21 and 22. According to particular embodiments, the suture staples 120 are configured to only partially penetrate a tubular tissue at its outer layer(s), e.g., they are not configured to penetrate through all layers of a bowel wall (unlike the surgical staples 114 (e.g. FIGS. 22-24) described herein that are configured to staple a specimen closed). In an embodiment, the suture staples 120 penetrate deep enough into the tubular tissue so that the suture 118 extending through the suture staples 120 can be held in place around the tissue. According to certain embodiments, the suture staples 120 are housed in a suture staple cartridge that may be disposable. For example, a disposable suture staple cartridge may be detachably coupled to each arm 104, 106 of the surgical device 102 (e.g., by snapping the suture staple cartridges into the arms prior to use during surgery), and then removed from each arm following surgery, after the suture staples 120 have been deployed. Alternatively, each arm 104, 106 may be disposable, wherein the arms 104, 106 are pre-loaded with suture staples 120 and discarded after surgery.

Figure 19:
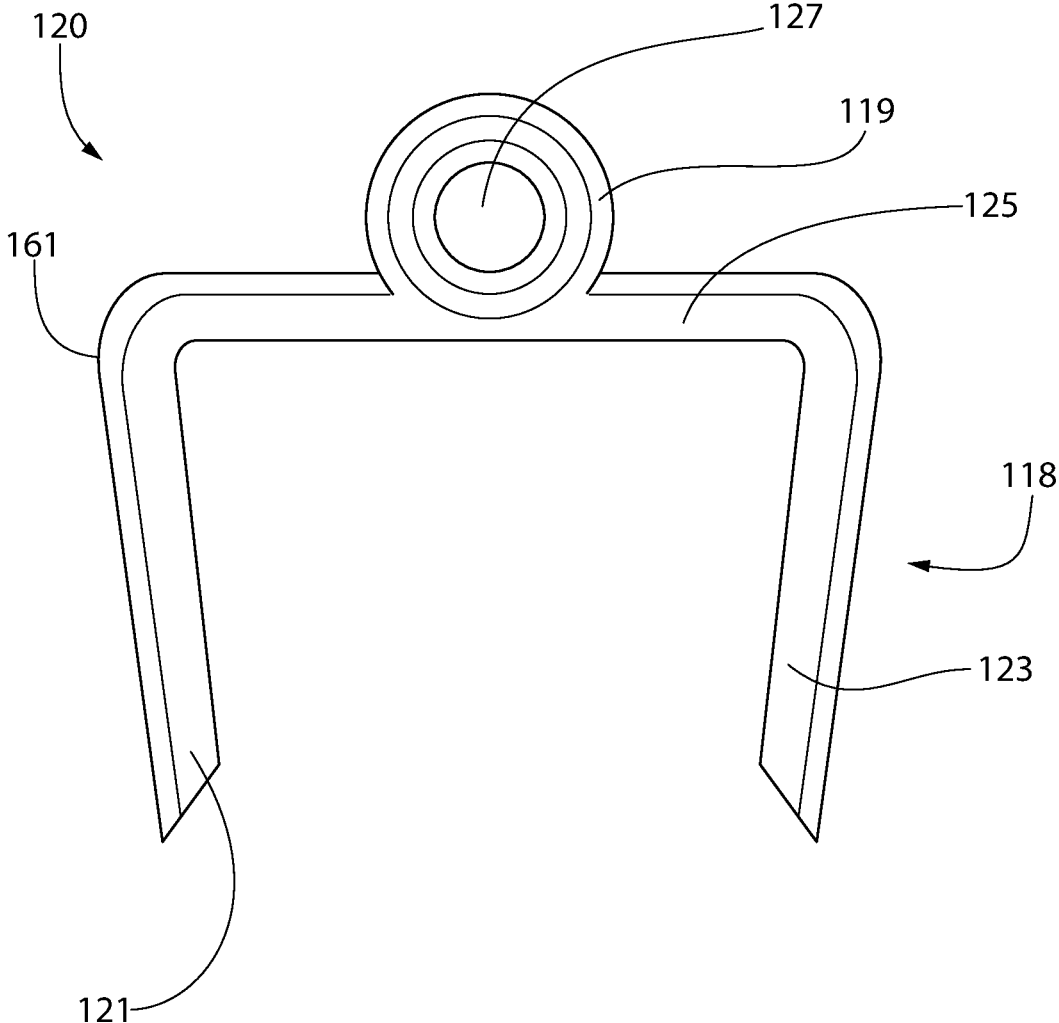
FIG. 19 is a partial view of a surgical staple that is housed in an arm of an exemplary surgical device in accordance with an exemplary embodiment of the present invention.
Figure 20:
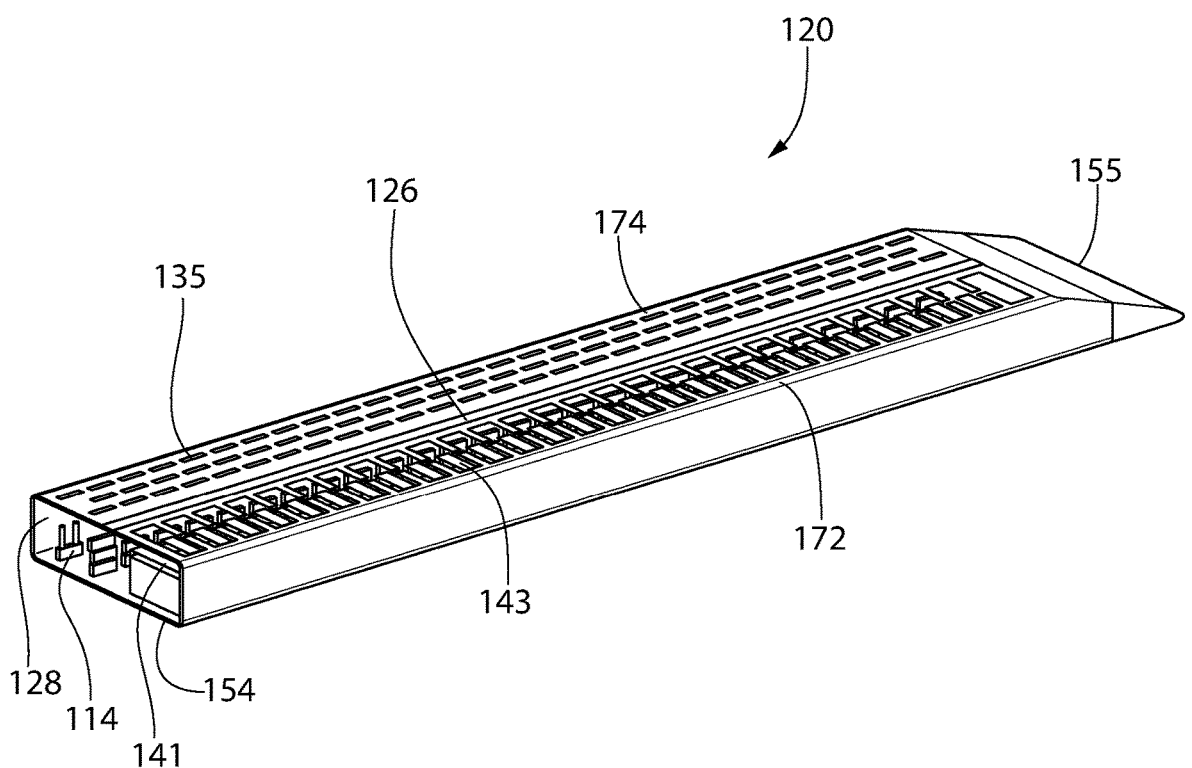
FIG. 20 is a perspective view of an arm of an exemplary surgical device in accordance with an exemplary embodiment of the present invention.

According to an embodiment illustrated in FIG. 19, each suture staple 118 has a staple body 161 comprising an elongated arm 125 comprising a loop 119 that defines an opening 127 at the center of the arm. The loop 119 provides the opening 127 or eyelet for receiving a suture. The suture staple body 161 may have a pair of legs 121, 123 that extend from opposite sides of the arm 125. Alternative embodiments of suture staples 120 are envisioned, wherein the suture 118 is threaded through the suture staples 120 according to other means.

Figure 24:
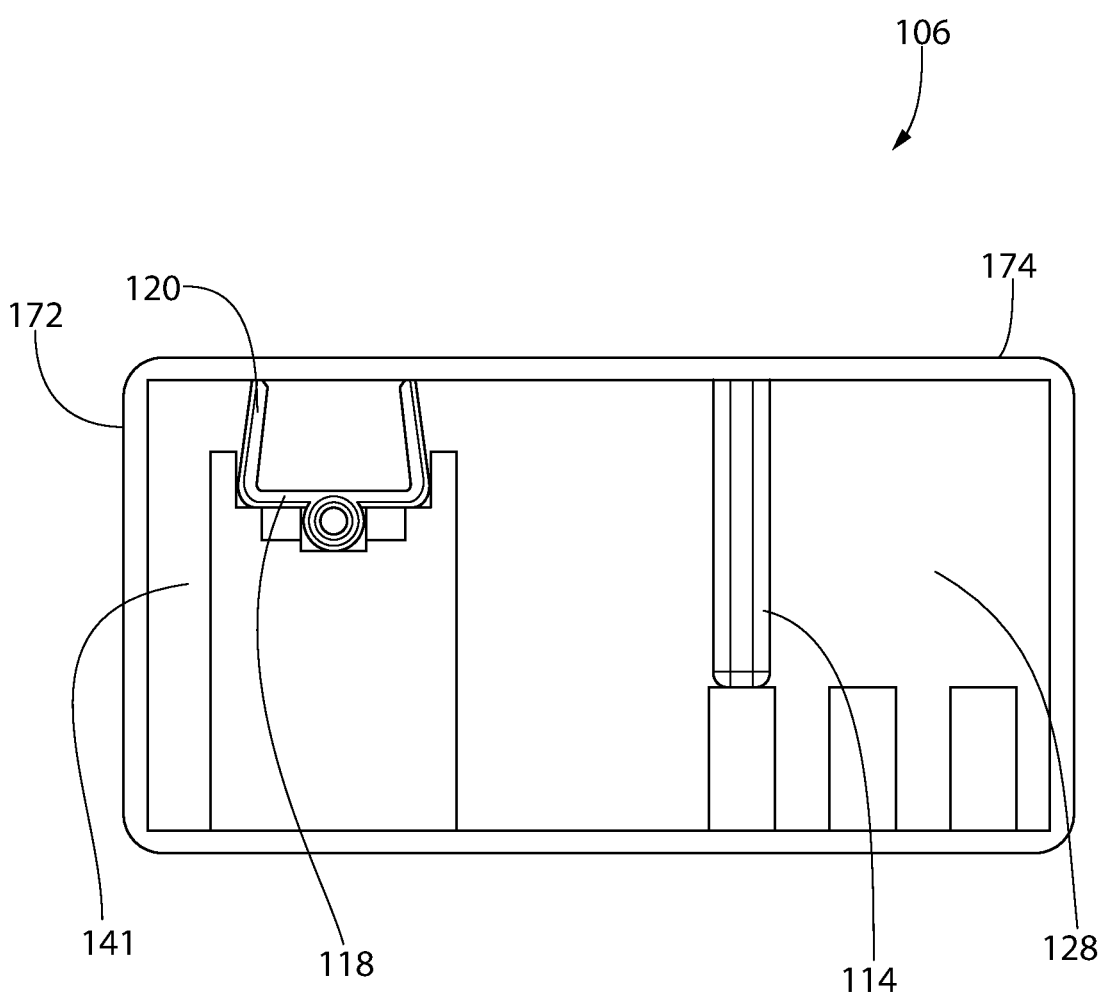
FIG. 24 is an illustration of an arm of an exemplary surgical device in accordance with an exemplary embodiment of the present invention.
Figure 25:
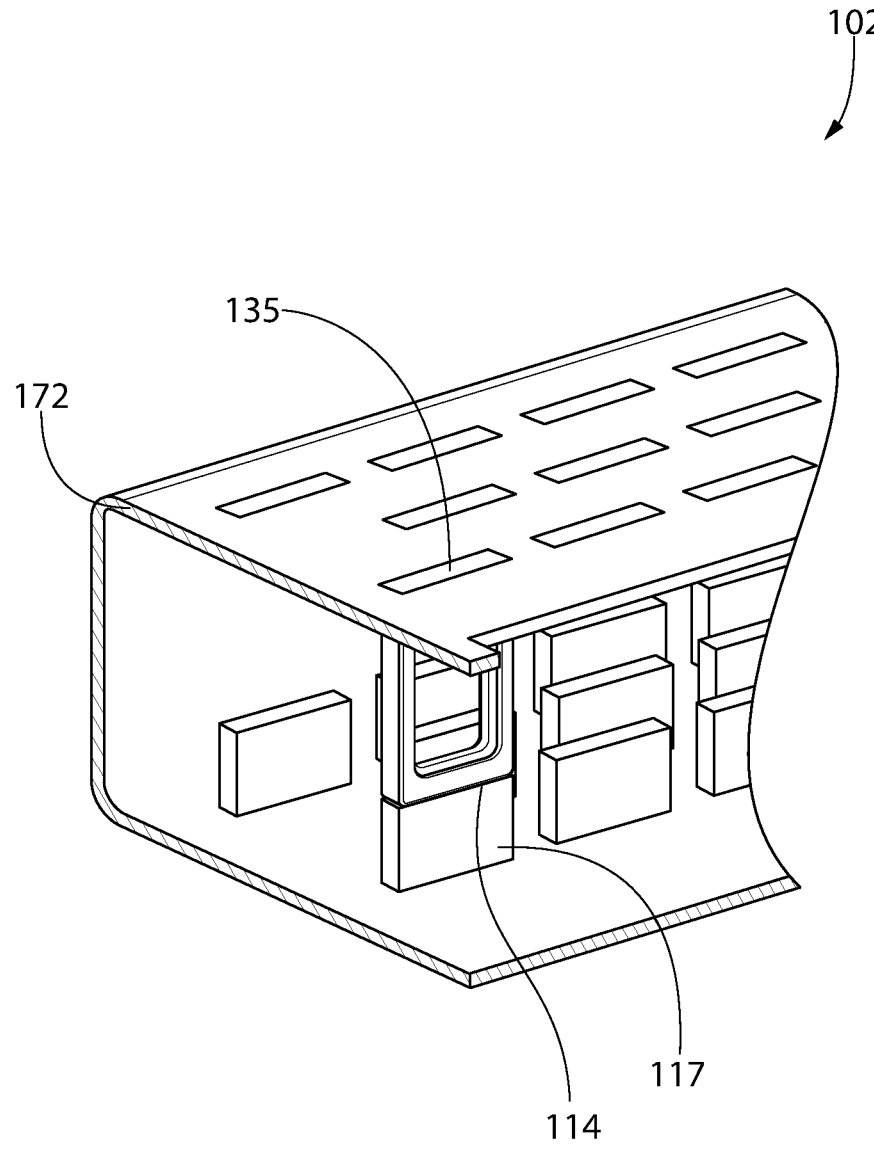
FIG. 25 is a partial top view of an arm of an exemplary surgical device in accordance with an exemplary embodiment of the present invention.
Figure 26:
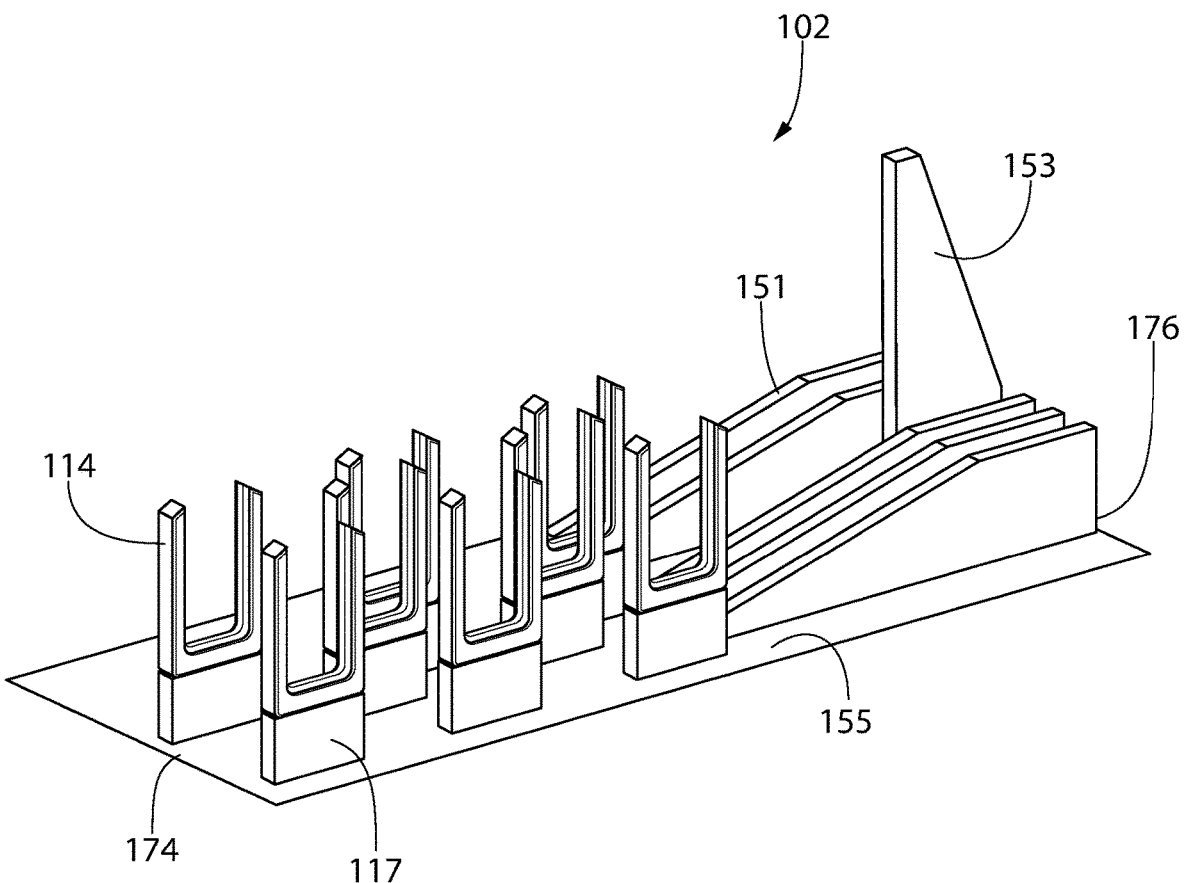
FIG. 26 is a partial view of an exemplary surgical device in accordance with an exemplary embodiment of the present invention.
Figure 27:
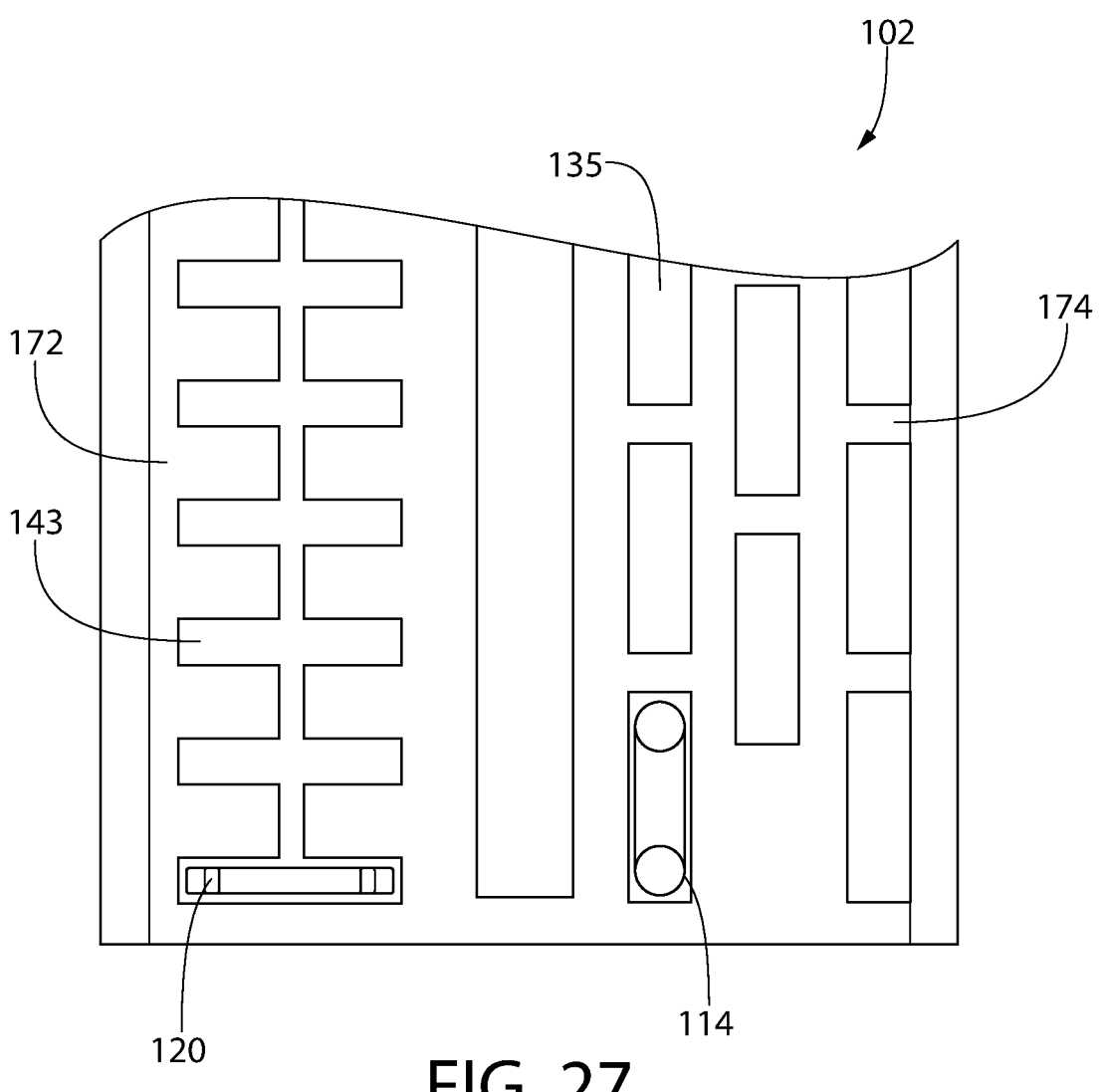
FIG. 27 is a top view of an arm of an exemplary surgical device in accordance with an exemplary embodiment of the present invention.
Figure 28:
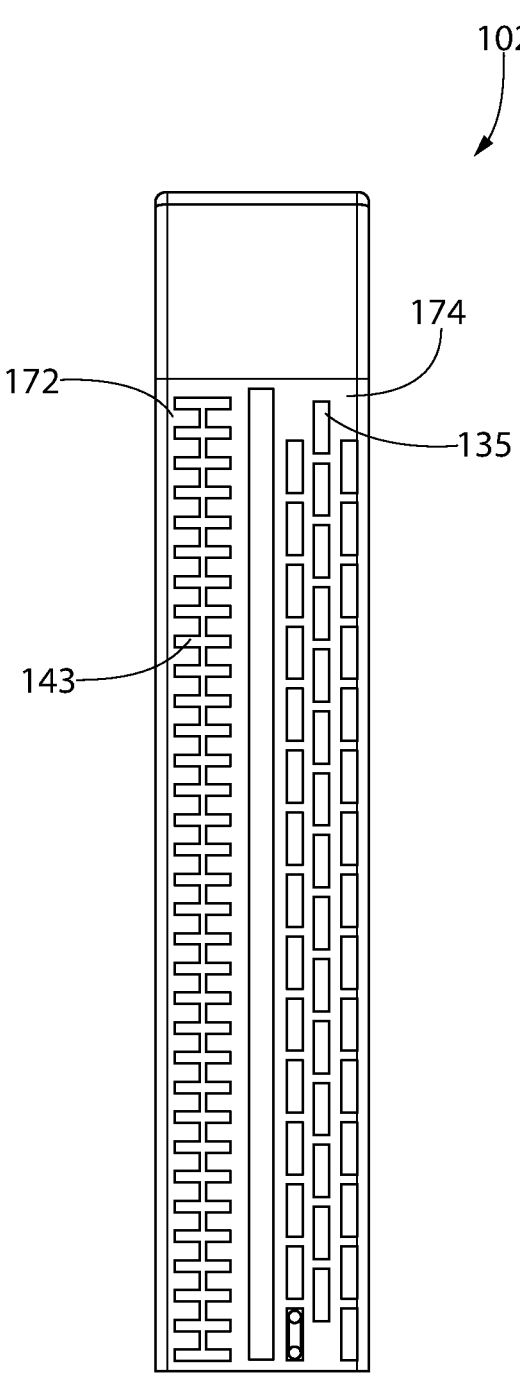
FIG. 28 is a partial view of a suture staple housed in an arm of an exemplary surgical device in accordance with an exemplary embodiment of the present invention.

Referring to FIG. 24, the surgical device 102 of the present invention may include a suturing mechanism 172 and a cutting mechanism 176. The cutting mechanism 176 comprises a cutting element 153 that is configured to transversely cut tubular tissue (e.g., transversely cut a bowel wall at a margin of resection), thereby exposing an open lumen. The cutting mechanism 176 may comprise a groove 155 extending along the longitudinal length of the first and/or second arm 104, 106, e.g., wherein the cutting element 153 comprises a knife blade movably disposed in the groove 155 and configured to move along the longitudinal length. The surgical device 102 may be configured so that the suturing mechanism 172 and cutting mechanism 176 can be actuated simultaneously or substantially simultaneously by a single actuation or motion by the surgeon, e.g., so that the suturing staples 120 are pushed into the tubular tissue at the same time as, immediately before, or immediately after the cutting element 153 cuts across the tubular tissue.

Referring to FIG. 22, each of the first arm 104 and the second arm 106 comprises a sled or sliding element 151 disposed underneath the suture staples 120, e.g., underneath the pushing mechanism 129 that is configured to push the suture staples 120. Embodiments of a sled or sliding element 151 are illustrated in FIGS. 22 and 24. The sled 151 may comprise a plurality of protrusions (e.g., angled protrusions) that are configured to slide underneath each protrusion of the pushing mechanism 129. Upon actuation by a surgeon (e.g., in response to an electrical signal from the actuation mechanism), the sliding element 151 is configured to slide longitudinally across each arm 104, 106 and push the suture staples 120 into the tubular tissue as it slides underneath them, e.g., underneath the pushing mechanism 129. The sliding element 151 may be coupled to the cutting element 153 (e.g., knife blade) in the first arm 104 and/or the second arm 106 so that the cutting element 153 slices the tissue as the sliding element 151 moves across the arm(s) 104, 106.

According to particular embodiments, the surgical device 102 of the present invention includes a suturing mechanism 172, a cutting mechanism 176 and a stapling mechanism 174. For example, a surgical stapler comprising cutting and stapling mechanism 174 may also include the suturing mechanism 172 of the present invention. According to an embodiment, the first arm 104 and second arm 106 of the surgical device 102 extend along a longitudinal axis 108, each of the suturing mechanism 172 and the stapling mechanism 174 being disposed along a side of the longitudinal axis 108 opposite to each other (e.g., they may be referred to as the suturing side 112 and stapling side 110 of the surgical device). In an embodiment, the cutting mechanism 176 is positioned along the longitudinal length between the suturing mechanism 172 and the stapling mechanism 174 (e.g., substantially along the longitudinal axis 108). As discussed herein, the stapling mechanism 174, suturing mechanism 172 and cutting mechanism 176 may be configured to be actuated simultaneously or substantially simultaneously by a single actuation or motion by the surgeon, e.g., so that the staples 114 (i.e., surgical staples configured to staple a tissue closed) and suture staples 120 are pushed into the tubular tissue at the same time as, immediately before, or immediately after the cutting element cuts across the tubular tissue.

Referring to FIGS. 22-28, the stapling mechanism 174 may comprise an interior portion 128 for housing the staples 114, and a plurality of staple slots 135 for permitting passage of the staples 114 out of the interior portion 128. The stapling mechanism 174 may comprise a pushing mechanism 117 configured to push the staples 114 toward the anvil 116 when the stapling mechanism 174 is actuated, e.g., when the sliding element 151 slides underneath the pushing mechanism 117. For example, the pushing mechanism 117 may comprise one or more protrusions disposed underneath each staple 114. The staples 114 are configured to contact the anvil 116 when the first arm 104 and the second arm 106 are in the clamped position. According to particular embodiments, the staples 114 are configured to penetrate all the way through a tubular tissue, e.g., through all layers of a bowel wall, and contact the anvil 116. The staples 114 may be arranged in a plurality of rows substantially parallel to each other (e.g., two rows, three rows, four rows, or five rows). For example, three rows of staples are shown in FIGS. 20, 25, and 27-28. According to certain embodiments, the staples 114 are housed in a staple cartridge that may be disposable. For example, a disposable staple cartridge may be detachably coupled to an arm of the surgical device 102 (e.g., by snapping the staple cartridge into the arm prior to use during surgery), and then removed from the arm following surgery, after the staples 114 have been deployed. Alternatively, each arm 104, 106 may be disposable, wherein one arm includes the anvil 116 and one arm is pre-loaded with staples 114, and the arms are discarded after surgery.

According to an embodiment, one or more disposable cartridges contain suture staples 118 and surgical staples 114, wherein the disposable cartridge(s) are detachably coupled to the arms 102, 104 prior to use (e.g., by snapping into the interior portions 128, 141 of the arms 102, 104). A sled or sliding element 151 may form part of the disposable cartridge(s) that contain the suture staples and surgical staples. A cutting element 153 may form part of the disposable cartridge, or may alternatively form part of an arm 102 or 104 of the surgical device. For example, the disposable cartridge(s) may comprise one or more grooves configured to receive a knife blade when detachably coupled to the arms 102, 104.

Referring to FIGS. 29A-31G, a suture clip applier 400 may be used for applying a suture 418 (e.g., pursestring suture) around a tubular tissue 407 adjacent to an open lumen 434. Before applying the suture 418, the tubular tissue is divided according to any known method that exposes the open lumen, e.g., with a surgical stapler, scissors, or the like. For example, the tubular tissue may be divided at a proximal and/or distal margin of resection. The suture clip applier 400 may be used in accordance with surgical methods described herein (e.g., laparoscopic or robotic methods). For example, the suture clip applier 400 may be inserted into a body cavity through a port incision and used to affix the suture around the open lumen of a tubular tissue after a conventional cutting mechanism (e.g., surgical knife, surgical scissors, surgical stapler, or the like) has been used to transversely divide the tissue and expose the open lumen.

Referring to FIGS. 29A-30C, a length of suture 418 (e.g., pursestring suture) comprising a pre-formed adjustable fastening 422 (e.g., a pre-formed knot, such as a pre-formed slipknot) is detachably coupled to the suture clip applier 400. This allows for tightening and closure of the suture 418 without the need to place a pursestring suture or tie a knot during surgery. Suture clips and suture staples described herein are both utilized as fasteners for holding a suture in place around a tubular tissue, e.g., a suture may be threaded through suture clips or suture staples. According to particular embodiments, the suture clips 406 can be configured to only partially penetrate a tubular tissue at its outer layer(s), or can be configured to penetrate through all layers of a bowel wall (similar to the surgical staples 114 described herein that are configured to staple a specimen closed). In an embodiment, the suture clips 406 penetrate deep enough into the tubular tissue so that the suture 418 extending through the suture clips 406 can be held in place around the tissue while closing the pursestring and drawing the tubular tissue into a closed position.

Figure 29A:
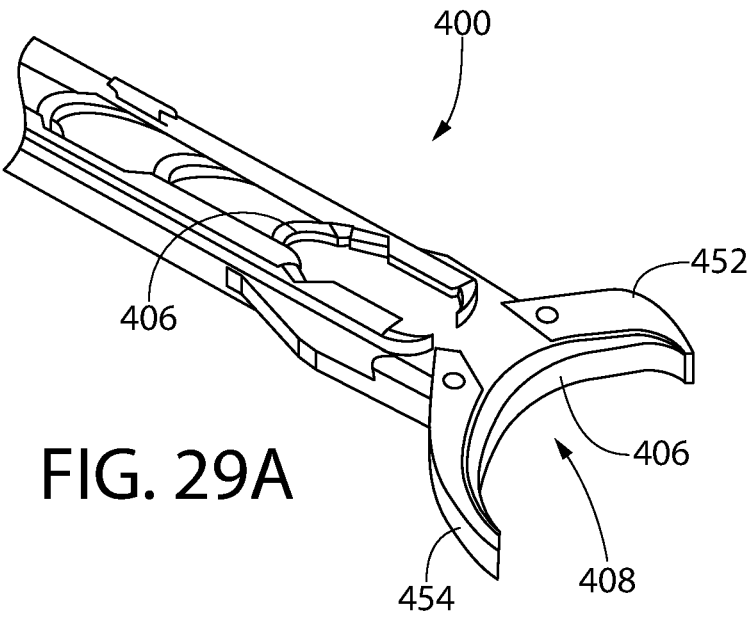
FIG. 29A-B is a perspective view of an exemplary surgical clip applier in accordance with an exemplary embodiment of the present invention.
Figure 29B:
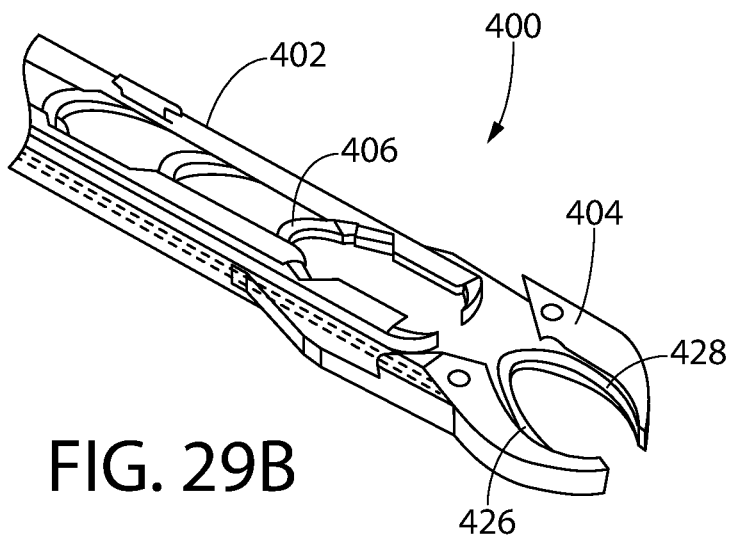
Figures 30A, 30B, 30C:
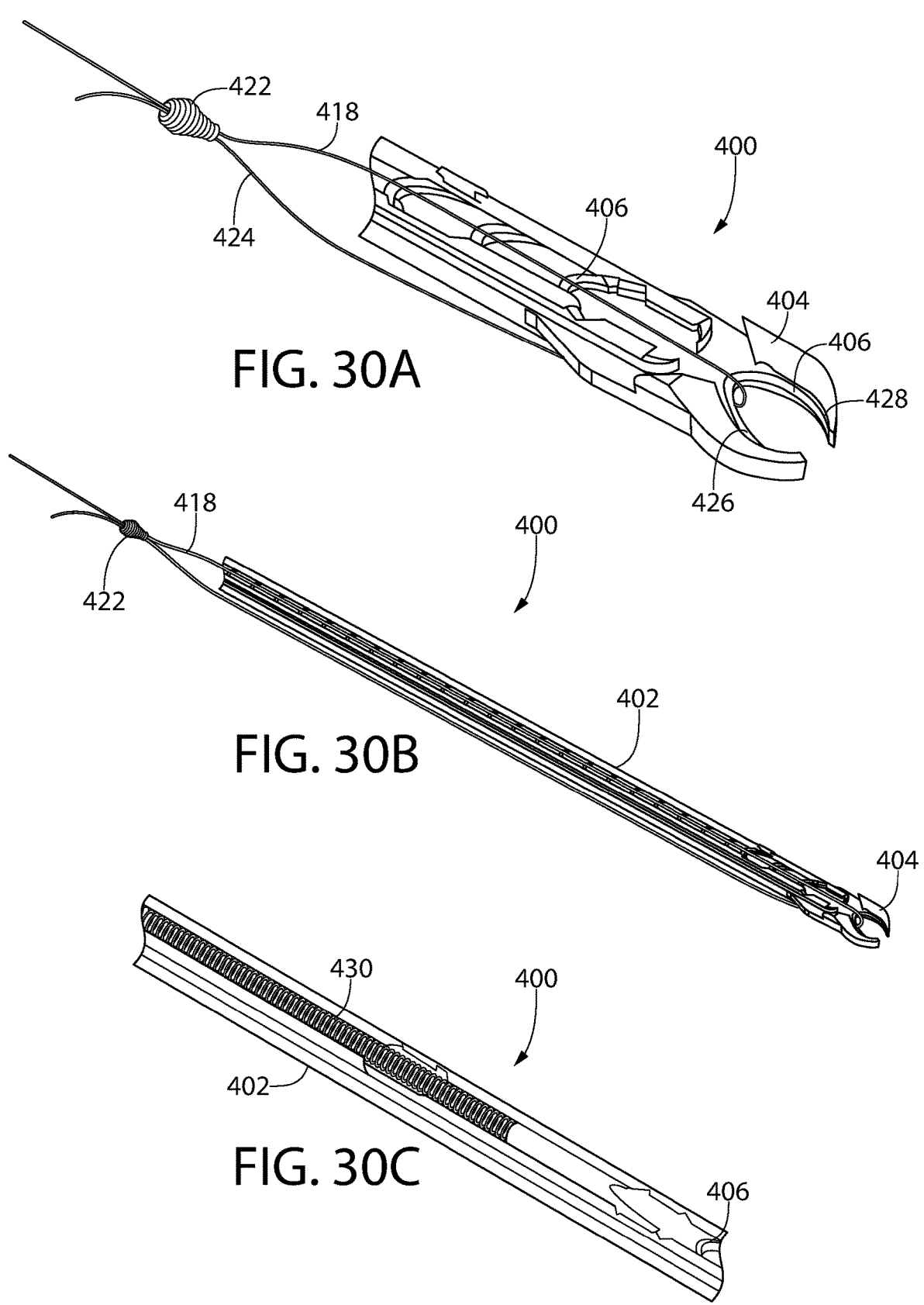
FIG. 30A-C is a perspective view of an exemplary surgical clip applier and suture in accordance with an exemplary embodiment of the present invention.
Figure 31A:
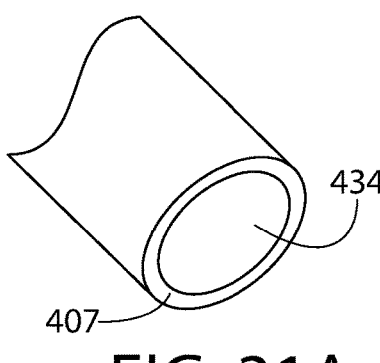
FIG. 31A-G is an illustration of an exemplary suture clip applier applying a suture and suture clips around an open lumen of a bowel wall in accordance with an exemplary embodiment of the present invention.
Figure 31B:
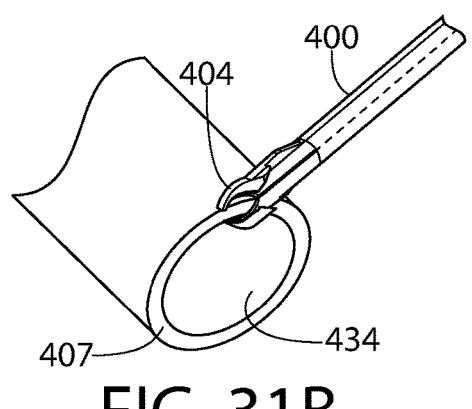
Figure 31C:
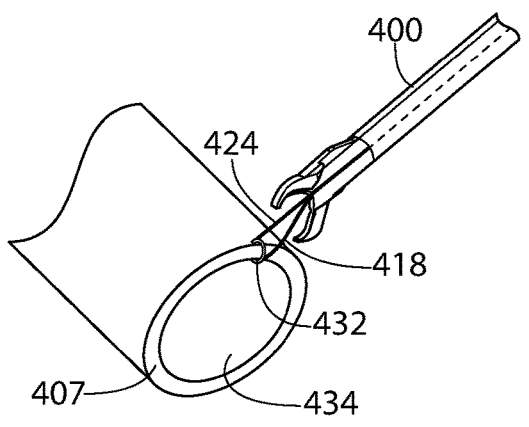
Figure 31D:
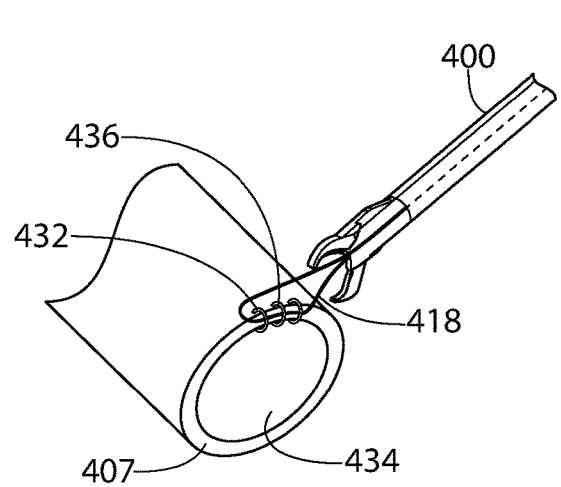
Figures 31E, 31F, 31G:
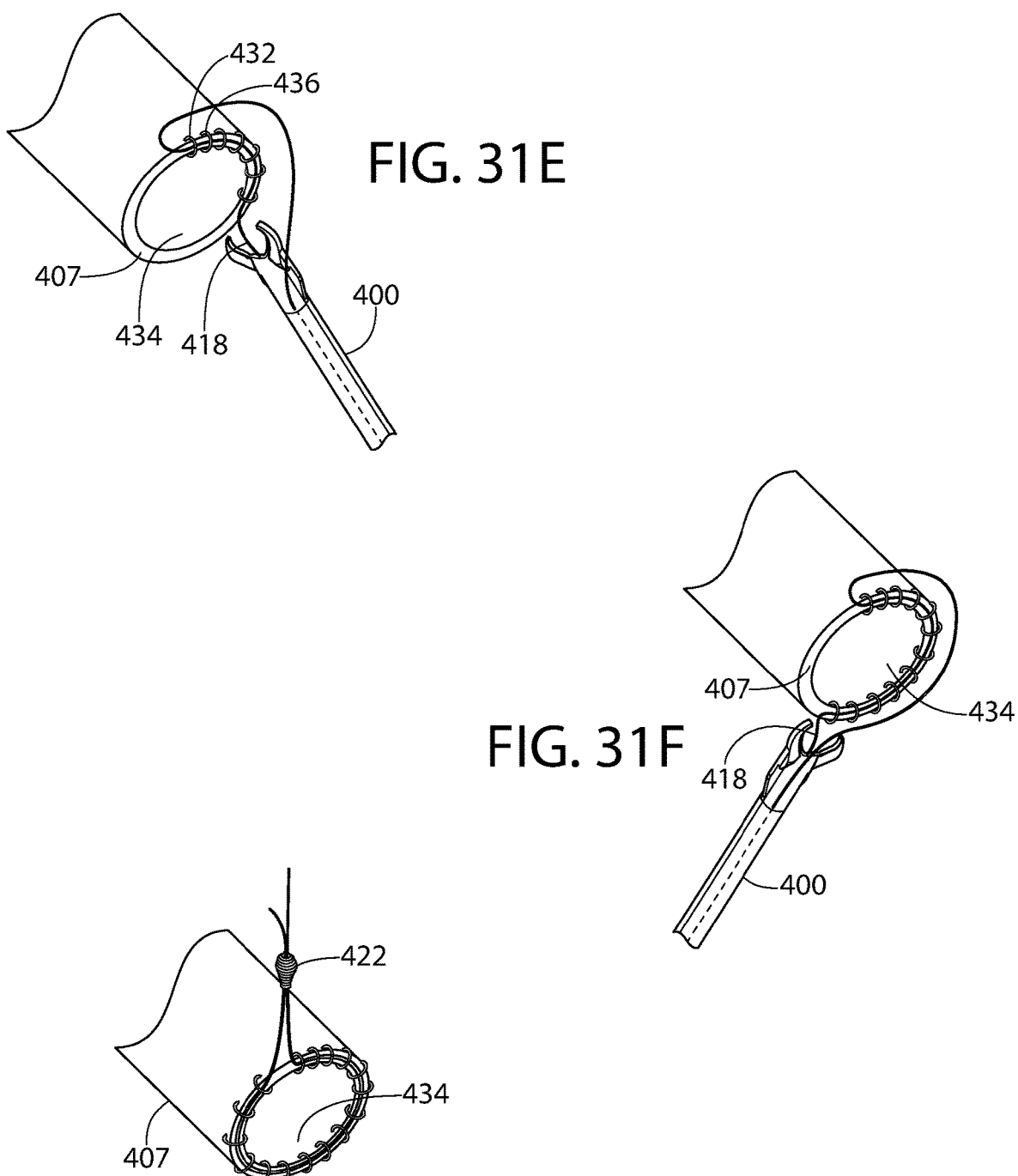

The suture clip applier 400 may comprise an elongated body 402 comprising a tissue clinching mechanism 404 at one end of the body 402, which is configured to deliver suture clips 406 to the tissue. The suture clip applier 400 can be inserted directly through a port incision, placed inside a casing to be used as part of a laparoscopic instrument, or placed into a casing to be used as part of a robotic instrument, e.g., da Vinci. The tissue clinching mechanism 404 may comprise two arms 452, 454 that are movable between an open position (e.g., as shown in FIG. 29A) and a closed or clinched position (e.g., as shown in FIG. 29B) as the arms 452, 454 expand and contract, respectively. For example, the two arms 452, 454 may be part of a single integral unit, or they may be separately formed arms that are hingedly connected to the elongated body. The suture clip applier 400 further comprises a plurality of deformable suture clips 406 mounted along a longitudinal length of the elongated body 402. According to an embodiment, the suture clip applier 400 is configured to be in the closed/clinched positon for insertion through a port or casing, prior to deployment of the suture clips 406, and to expand into an open position in which the two arms 452, 454 extend across the open edge of the bowel wall.

According to an embodiment, each deformable suture clip 406 has two legs 426, 428 configured to penetrate tubular tissue; for example, each suture clip 406 may be shaped into a curvature with two ends configured to penetrate tubular tissue. Each suture clip 406 may be configured to be detachably positioned within an interior 408 of the two arms 452, 454 and to be deformed between open and clinched positions in response to the two arms 452,454 being moved between the open and clinched positions. Any number of deformable suture clips 406 suitable for placing a suture around an open lumen may be included along the elongated body 402. For example, there may be between 4-20 suture clips 406, between 6-20 suture clips 406, between 8-20 suture clips 406, between 6-15 suture clips 406, between 8-15 suture clips 406, between 6-12 suture clips 406, between 8-12 suture clips 406, or between 6-10 suture clips

406 mounted along the longitudinal length of the elongated body 402. A length of the suture 418 comprises a pre-formed adjustable fastening (e.g., a pre-formed knot, such as a pre-formed slipknot) 422 and a loop 424 extending from the pre-formed adjustable fastening 422, an interior of the loop extending between the two arms 452,454 of the clinching mechanism 404. When a deformable suture clip 406 is in ready position (i.e., positioned within the interior of the two arms 452, 454 of the clinching mechanism 404), the interior of the loop extends between two legs 426, 428 of the suture clip 406.

According to an embodiment, the suture clip applier 400 comprises one or more biasing elements 430 configured to longitudinally advance each deformable suture clip 406 toward the tissue clinching mechanism 404. For example, the biasing element 430 may comprise one or more springs. The biasing element 430 may be configured to automatically advance each deformable suture clip 406 toward the tissue clamping mechanism 404 in response to a deformable suture clip 406 being released from the clinching mechanism 404. Other configurations to advance the suture clip 406, such as a spring system, pulley system and/or other mechanical system may be used.

According to an embodiment, a suturing system comprising the suture clip applier 400 may be connected to an actuating mechanism (e.g., mechanically and/or electrically and/or remotely via computer), which means that the actuating mechanism is in communication with the suture clip applier 400 so that it can actuate the suture clip applier 400 to affix each suture clip 406 to the tissue, e.g., via mechanical and/or electrical and/or remote means controllable by a surgeon.

An embodiment of a method for using the clip applier to apply a suture adjacent to an open lumen in a tubular tissue is illustrated in FIGS. 31A-31G. According to particular embodiments, the method comprises actuating the tissue clinching mechanism 404 to clinch a first deformable suture clip 432 onto the tubular tissue at a first position adjacent to the open lumen 434 (i.e., to insert the clip into the tissue around the edge of the open lumen), a portion of the suture loop 418 extending through the first deformable suture clip 432 (between the tubular tissue and the suture clip). The tissue clinching mechanism 404 is opened after the first suture clip 432 is applied to the tissue, and moved to the second position. Each subsequent position (first, second, third, fourth, fifth, etc.) is positioned in sequential order around the tubular tissue, so that the first position is next to the second position, the third position is next to the second position, the fourth position is next to the third position, etc. The first clip 432 is applied at the first position, the second clip 436 is applied at the second position, the third clip is applied at the third position, etc.

After the first suture clip 432 is affixed to the tissue at the first position, a second suture clip 436 is advanced by the biasing element 430 into the ready position at the interior of the arms 452, 454 of the clinching mechanism 404. Advancing the next suture clip may occur automatically or in response to an actuation by the surgeon. The tissue clinching mechanism 404 is activated to clinch the second deformable suture clip 436 onto the tubular tissue at the second position, a portion of the suture loop 418 extending through the first suture clip 432 and second suture clip 436 (between the tubular tissue and the suture clips). The process continues to sequentially affix a series of the deformable suture clips 406 around the open lumen (e.g., between 4-20 suture clips 406, between 6-20 suture clips 406, between 8-20 suture clips 406, between 6-15 suture clips 406, between 8-15 suture clips 406, between 6-12 suture clips 406, between 8-12 suture clips 406, between 6-10 suture clips 406) by actuating the tissue clinching mechanism 404 to clinch each deformable suture clip 406 onto the tubular tissue at a plurality of positions around the open lumen. After the suture clips 406 are applied to the tissue, the suture 418 forms a loop that extends from the pre-formed adjustable fastening 422 and through the deformable suture clips 406 affixed to the tubular tissue (between the tubular tissue and suture clips 406). The suture 418 detaches from the suture clip applier 400, e.g., automatically or in response to an actuation by the surgeon. The suture 418 may then be tightened to draw the lumen closed according to embodiments described herein (e.g., by pulling an end portion of the suture, or the like).

The following example further illustrates embodiments of the methods disclosed herein.

EXAMPLE

The embodiments encompassed herein are now described with reference to the following example. The example is provided for the purpose of illustration only and the disclosure encompassed herein should in no way be construed as being limited to this example, but rather should be construed to encompass any and all variations which become evident as a result of the teachings provided herein.

Example 1: Natural Orifice Intracorporeal Anastomosis with Transrectal Extraction The following methods of bowel division and natural orifice intracorporeal anastomosis with transrectal extraction are performed without the use of an abdominal wall incision (only port incisions are used), in a stepwise approach designed for a robotic platform. The following steps are performed once the diseased portion of the bowel has been mobilized and the mesentery of this portion has been divided.

Figure 2:
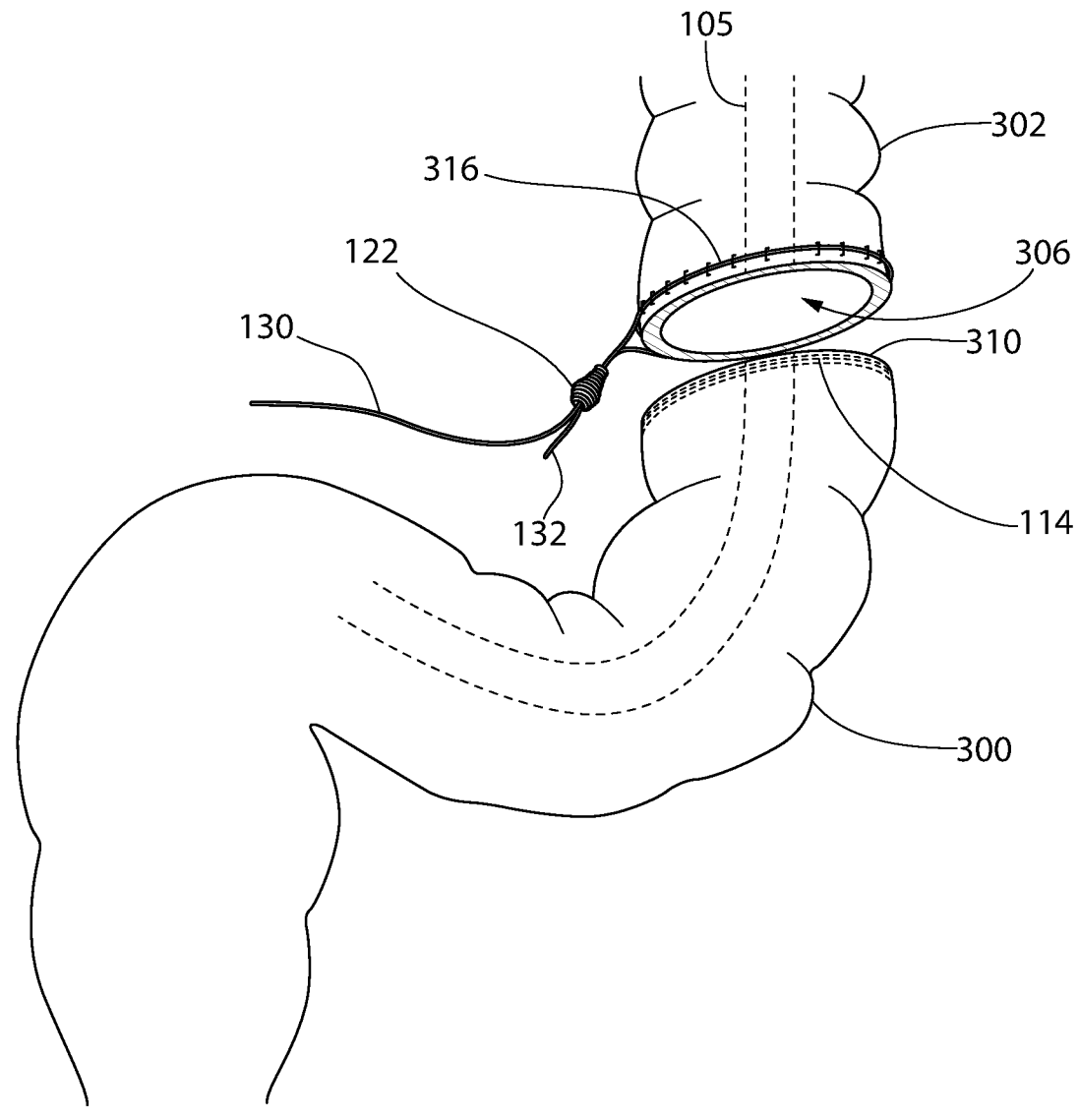
FIG. 2 is an illustration of a bowel wall that has been divided at a proximal margin of resection in accordance with an exemplary embodiment of the present invention.
Figure 3:
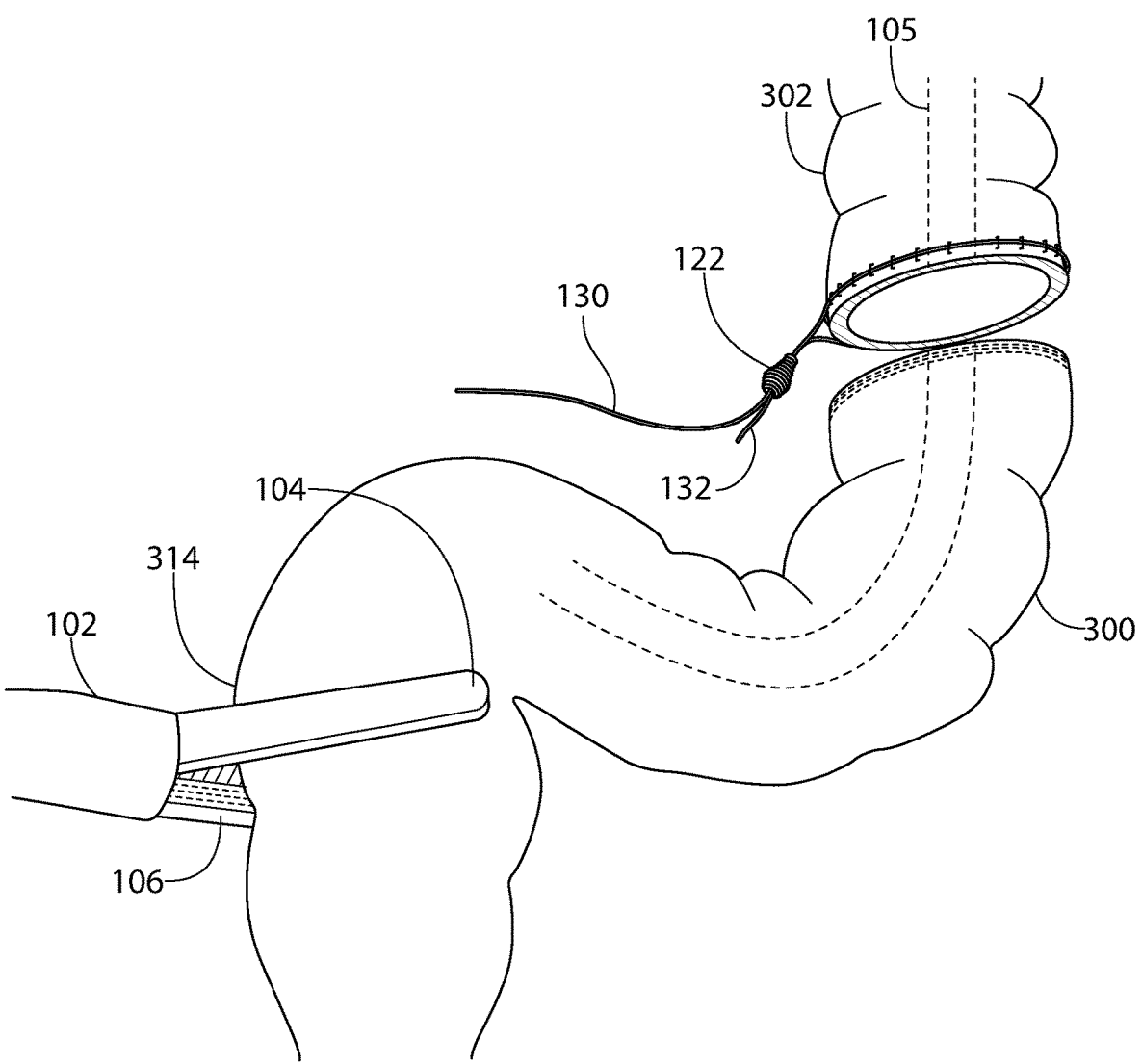
FIG. 3 is an illustration of a bowel wall being divided at a distal margin of resection by a surgical device in accordance with an exemplary embodiment of the present invention.

Step 1: The surgical device 102 (having a suturing mechanism 172 (FIG. 22), cutting mechanism 176 (FIGS. 22 and 26) and stapling mechanism 174 (FIG. 26) as described herein) is placed across the bowel wall at the proposed proximal margin of resection 312 (FIG. 1) and deploys a closed linear staple line across the side of the specimen 300 and attaches a pursestring suture with a slip-knot 122 to the proximal bowel portion 302 (FIG. 2). As an alternative, the bowel is divided by any known method and the suture clip applier 400 described herein is used to apply a pursestring suture on the open proximal bowel portion 302.

Figure 4:
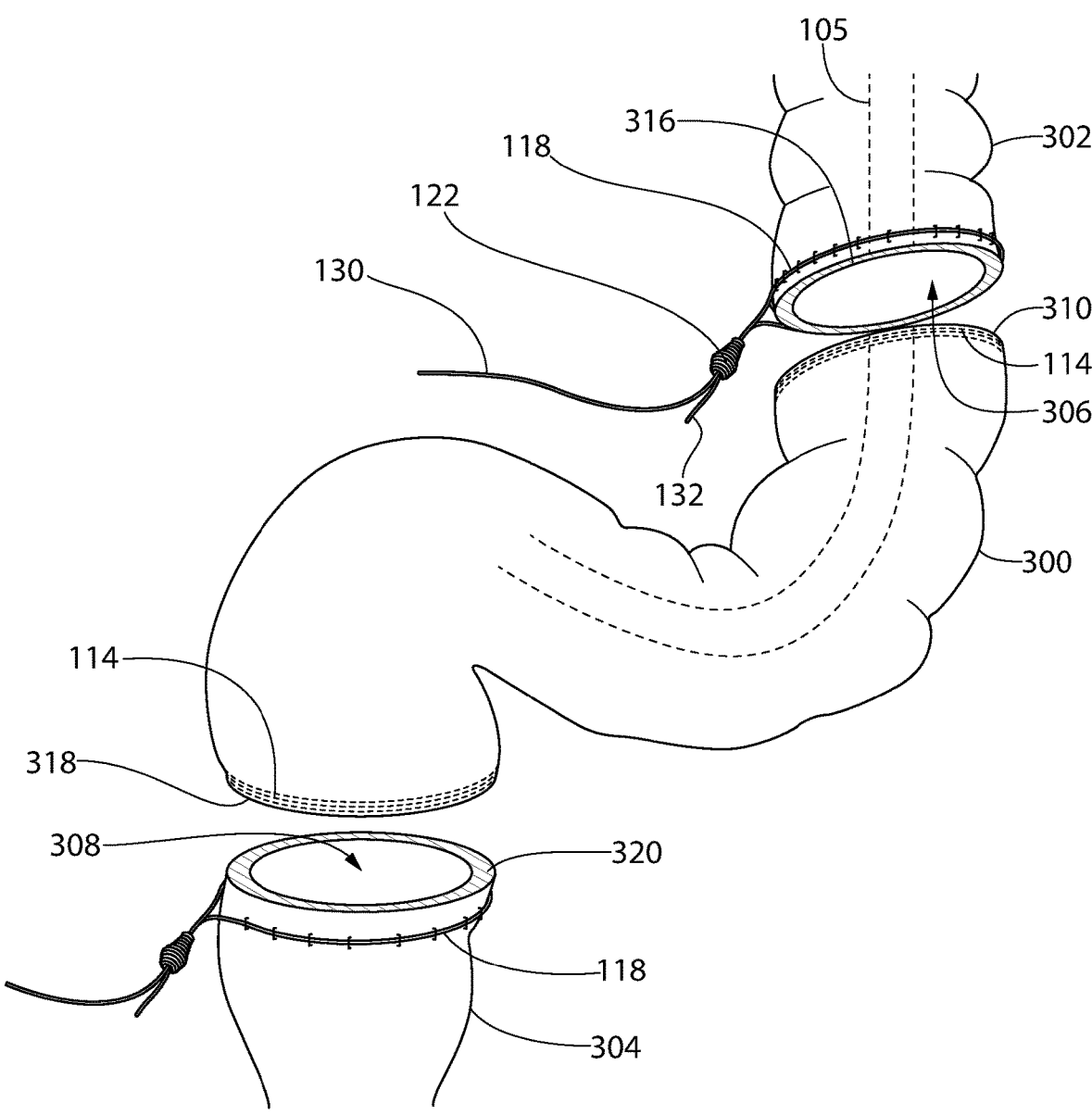
FIG. 4 is an illustration of a bowel wall that has been divided at proximal and distal margins of resection in accordance with an exemplary embodiment of the present invention.
Figure 5:
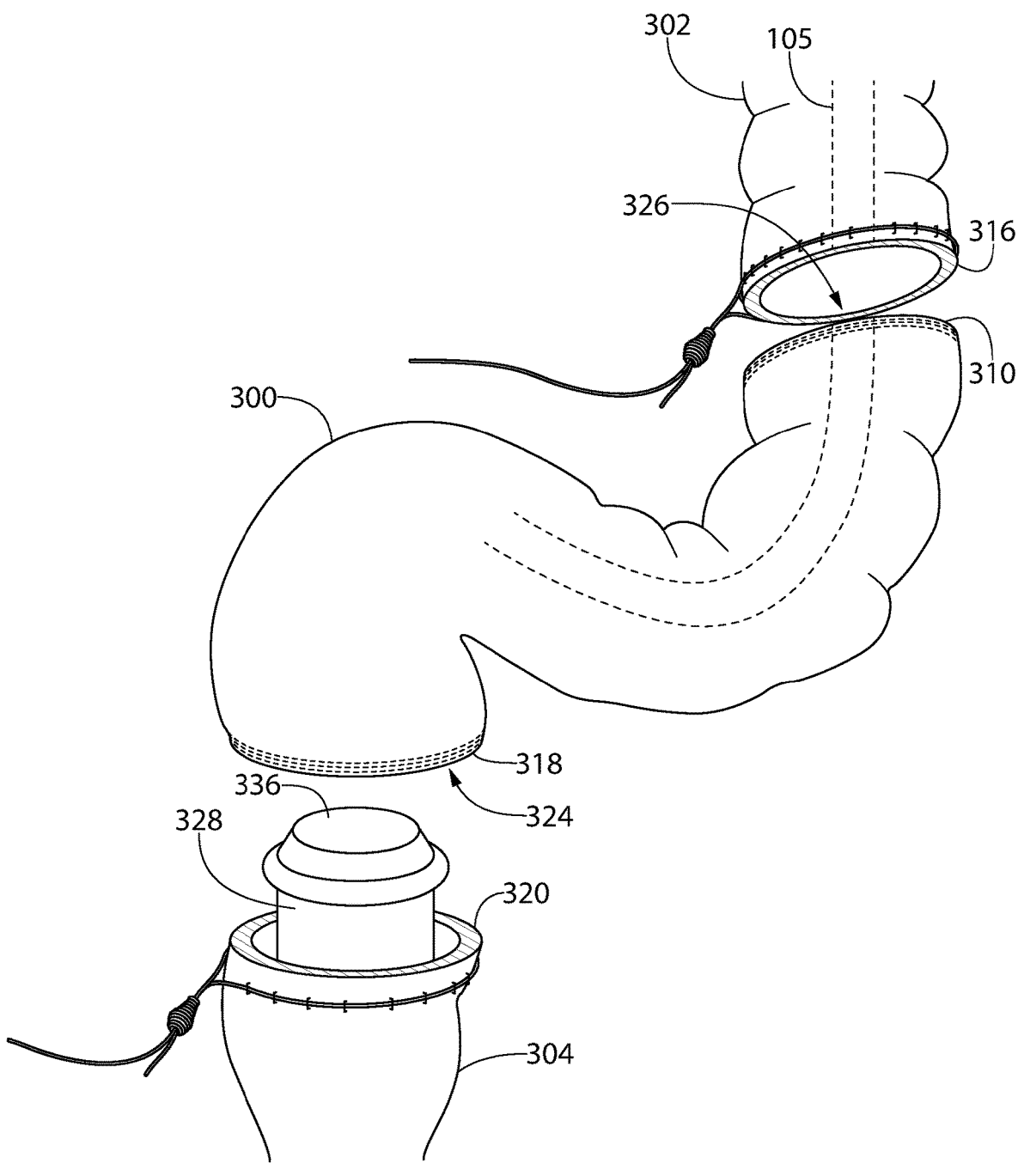
FIG. 5 is an illustration of an exemplary a rectal extractor attached to an exemplary circular stapler in accordance with an exemplary embodiment of the present invention.

Step 2: The surgical device 102 is placed across the bowel wall at the proposed distal margin of resection 314 (FIG. 3) and deploys a closed linear staple line across the side of the specimen 300 and attaches a pursestring suture with a slip-knot 122 to distal bowel portion 304 (FIG. 4). As an alternative, the bowel is divided by any known method and the suture clip applier 400 described herein is used to apply a pursestring suture on the open distal bowel side.

Figure 6:
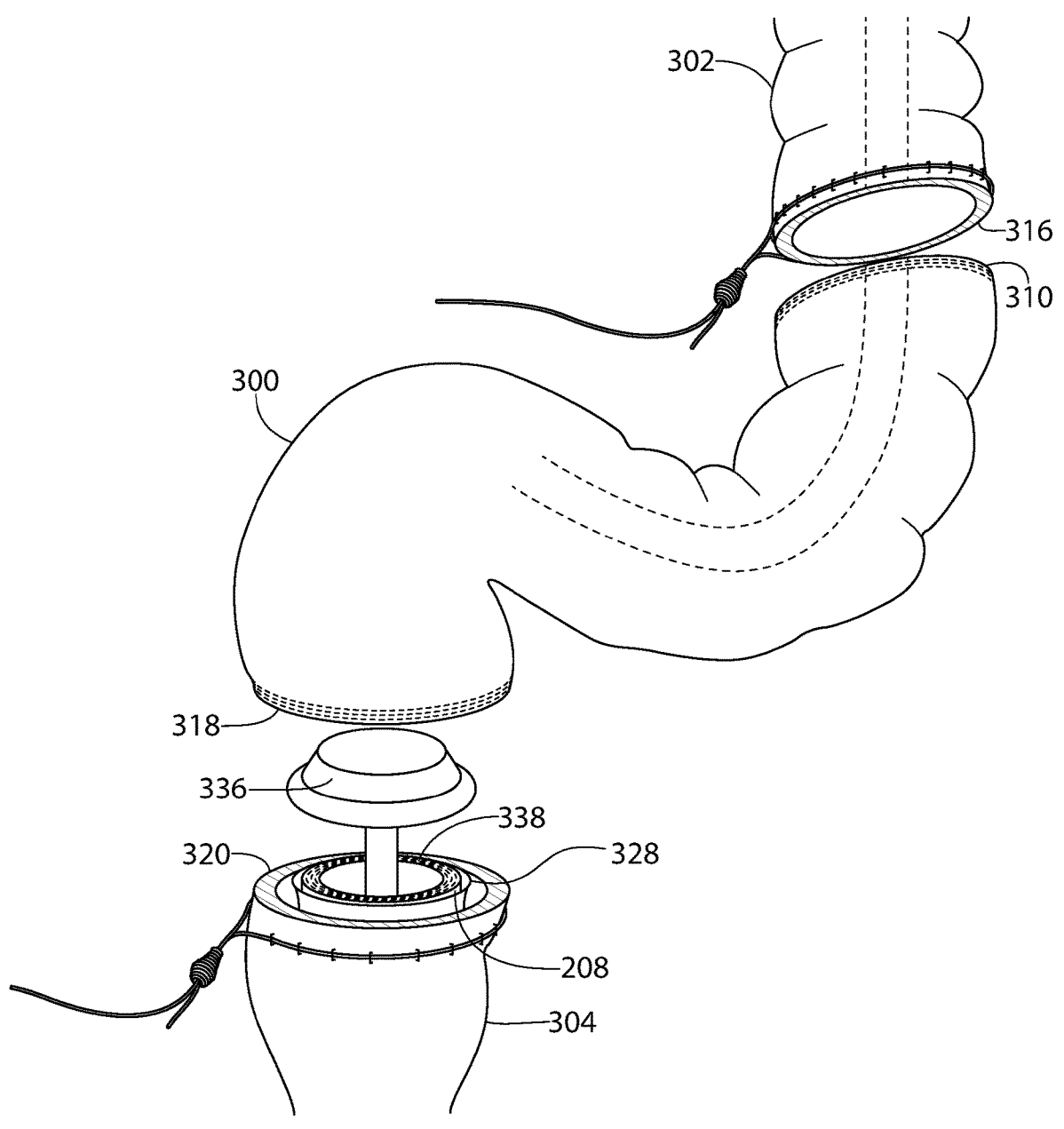
FIG. 6 is an illustration of an exemplary rectal extractor attached to an exemplary circular stapler in accordance with an exemplary embodiment of the present invention.

Step 3: A self-expandable transrectal retractor 328 is then introduced through the natural orifice of the rectum with the aid of the circular stapler (FIG. 5) and is deployed (FIG. 6). Once completely expanded, it serves to dilate the rectal stump and protect the bowel wall while the specimen 300 is extracted.

Figure 7:
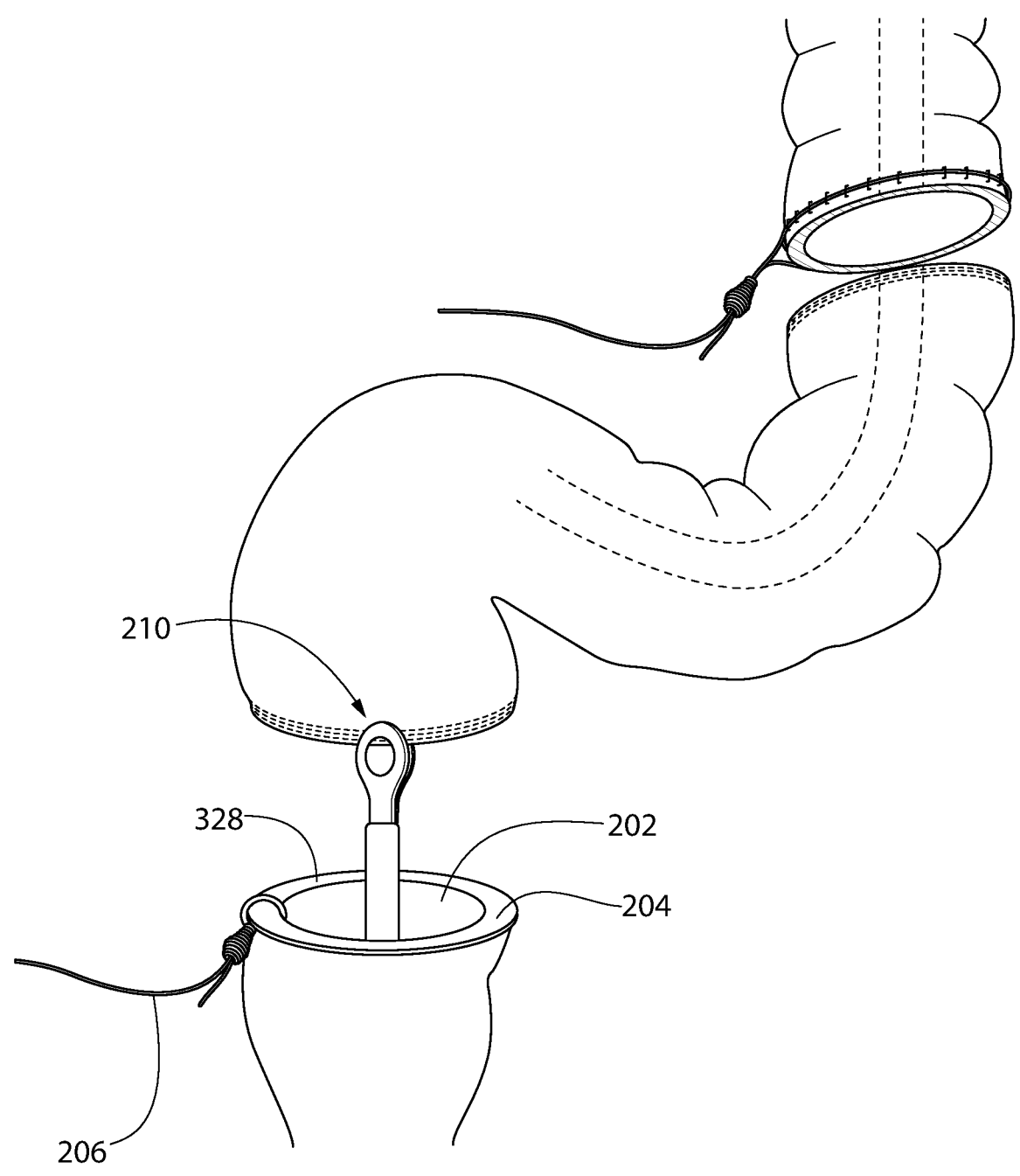
FIG. 7 is an illustration of an exemplary use of a rectal extractor and grasping tool in accordance with an exemplary embodiment of the present invention.

Step 4: A grasping tool 210 or other grasping forceps or endo bag is placed through the transrectal retractor 328 and grasps the specimen 300 (FIG. 7). The specimen 300 is extracted transrectally through the transrectal retractor 328

Figure 8:
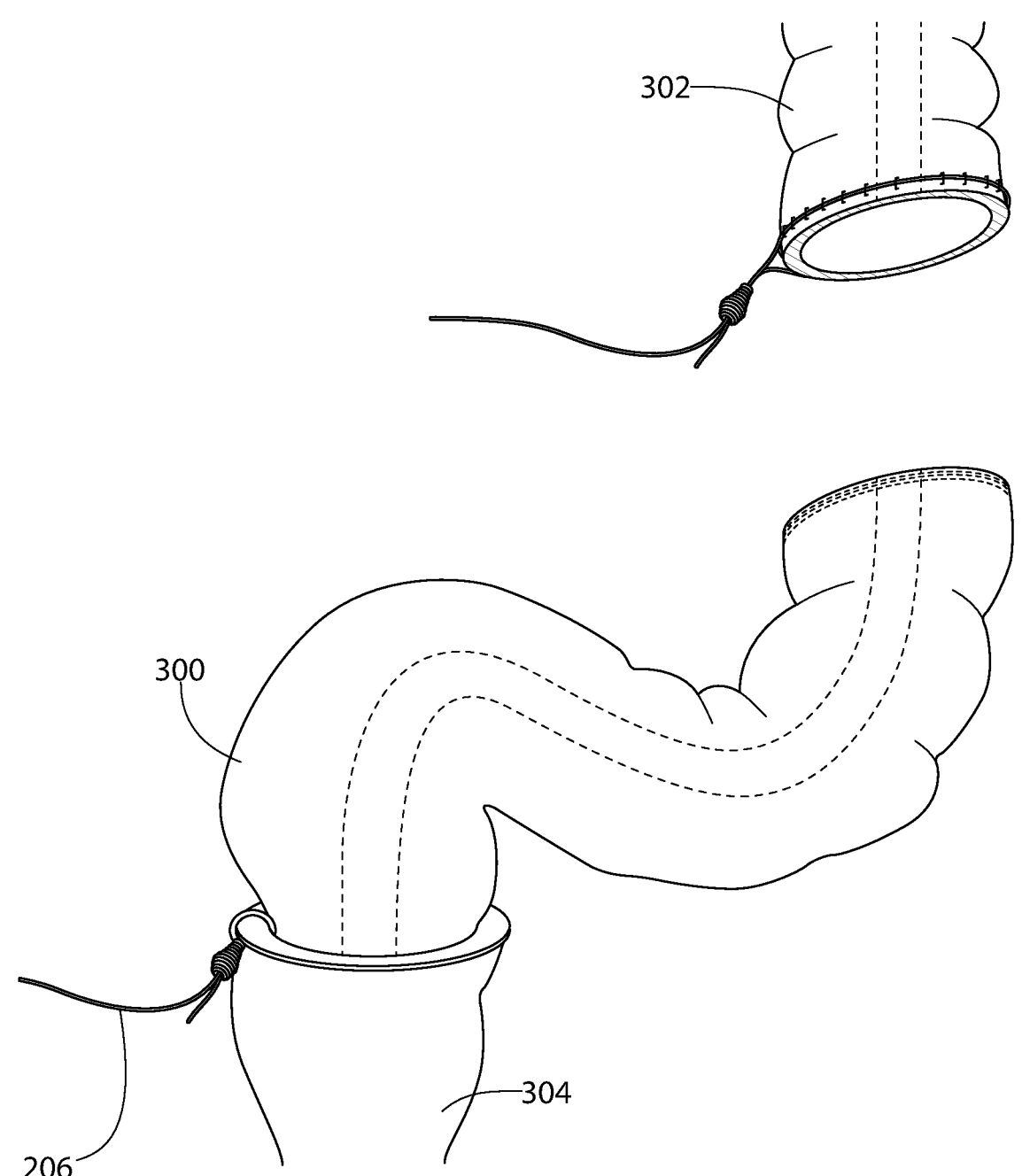
FIG. 8 is an illustration of an exemplary use of a transrectal extraction of a specimen in accordance with an exemplary embodiment of the present invention.

(FIG. 8). The transrectal retractor 328 is then removed with the aid of a drawstring (FIG. 9).

Step 5: A circular anastomotic stapler 334 is inserted via the anus into the distal bowel portion 304 with the anvil 336 connected to the head component. The anvil 336 is pushed forward through the interior lumen 308 of the distal bowel portion 304 into the abdominal cavity (FIG. 10).

Step 6: The anvil 336 is detached and inserted into the interior lumen 306 of the proximal bowel portion 302. The bowel wall tissue 316 is drawn into the shaft of the anvil 336 by tightening and securing the pursestring via the slip-knot (FIG. 11).

Step 7: The open end of the distal bowel edge 320 is drawn into the head component around the central trocar shaft 332 by tightening and securing the pursestring with the aid of the slip-knot (FIG. 12).

Step 8: The anastomosis 322 is formed. The anvil 336 is pulled towards the head component. The circular stapler 334 is then closed to couple the anvil 336 to the head, until the desired position. A circular stapled anastomosis 322 is then fashioned cutting off the ends of the proximal bowel portion 302 and the distal bowel portion 304 that have been drawn into the stapler device along with the pursestring suture (FIG. 13).

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

What is claimed is:

1. A method of using a surgical device to intracorporeally resect a bowel specimen from a subject, the surgical device comprising:

a first arm and a second arm each having a longitudinal length with opposite proximal and distal end portions, at least one of said first arm and said second arm being movable between an open position and a clamped position, wherein the surgical device includes a suturing mechanism comprising:

a first row of suture staples positioned along the longitudinal length in said first arm, and a second row of suture staples positioned along the longitudinal length in said second arm; and a length of suture comprising first and second end regions coupled together by a pre-formed adjustable fastening held in the surgical device, a first threaded region of the suture extending through the first row of suture staples, a second threaded region of the suture extending through the second row of suture staples, a first unthreaded region extending along the longitudinal length of said first arm, and a second unthreaded region extending along the longitudinal length of said second arm;

the method comprising:

clamping the first arm and the second arm over a proximal margin of resection between the specimen and a healthy bowel portion;

actuating a cutting mechanism to divide the bowel at the proximal margin of resection, actuating a stapling mechanism to close an interior lumen of the specimen by applying the staples to a proximal edge portion of the specimen;

actuating the suturing mechanism to attach the first and second rows of suture staples to an edge portion of the proximal bowel portion, wherein the suture comprising the pre-formed adjustable fastening detaches from the surgical device and forms a loop around the edge portion of the proximal bowel portion, a portion of the suture extending through the suture staples; and clamping the first arm and the second arm over a distal margin of resection between the specimen and a healthy bowel portion;

actuating the cutting mechanism to divide the bowel at the distal margin of resection, actuating the stapling mechanism to close an interior lumen of the specimen by applying the staples to a distal edge portion of the specimen;

actuating the suturing mechanism to attach the first and second rows of suture staples to an edge portion of the distal bowel portion, wherein the suture comprising the pre-formed adjustable fastening detaches from the surgical device and forms a loop around the edge portion of the distal bowel portion, a portion of the suture extending through the suture staples; and, extracting the sample specimen through the subject's rectum, wherein the extracting comprises the steps of transanally inserting a grasping tool through the distal bowel portion, grasping the specimen with the grasping tool and extracting the specimen through the subject's rectum.

2. The method according to claim 1, wherein actuating the cutting mechanism, actuating the stapling mechanism and actuating the suturing mechanism occur simultaneously, or substantially simultaneously, in response to a single actuation by a surgeon.

3. The method according to claim 1 further comprising: intracorporeally forming an anastomosis between the proximal bowel portion and the distal bowel portion, wherein intracorporeally forming the anastomosis comprises transanally inserting a circular stapler and advancing the circular stapler through the distal bowel portion, the circular stapler comprising a stapling cartridge and an anvil component removably coupled hereto.

4. The method according to claim 1, wherein the pre-formed adjustable fastening together with the length of suture is configured to form a loop around the edge portion of the distal bowl portion.

5. The method according to claim 1, wherein the pre-formed adjustable fastening detaches from within a shaft of the surgical instrument such that the pre-formed adjustable fastening is released between the first arm and the second arm.

6. A method of intracorporeally resecting a bowel specimen from a subject, the method comprising:

clamping a first arm and a second arm over a proximal margin of resection between the specimen and a healthy bowel portion;

actuating a cutting mechanism to divide the bowel at the proximal margin of resection tranversally across a lumen, actuating a stapling mechanism to close an interior lumen of the specimen by applying the staples to a proximal edge portion of the specimen;

actuating a suturing mechanism to attach a first and a second row of suture staples to an edge portion of the proximal bowel portion, wherein the suture comprises a pre-formed adjustable fastening, wherein the fastening detaches from the surgical device and forms a loop around the edge portion of the proximal bowel portion, a portion of the suture extending through the suture staples; and clamping the first arm and the second arm over a distal margin of resection between the specimen and a healthy bowel portion;

actuating the cutting mechanism to divide the bowel at the distal margin of resection transversally across the lumen, actuating a stapling mechanism to close an interior lumen of the specimen by applying the staples to a distal edge portion of the specimen;

actuating the suturing mechanism to attach the first and second rows of suture staples to an edge portion of the distal bowel portion, wherein the suture comprising the pre-formed adjustable fastening detaches from the surgical device and forms a loop around the edge portion of the distal bowel portion, a portion of the suture extending through the suture staples; and, extracting the specimen having a lumen through the subject's rectum before connecting the distal and proximal bowel portions by the formation of an anastomosis, wherein the extracting comprises the steps of transanally inserting a grasping tool through the distal bowel portion, grasping the specimen having a lumen with the grasping tool and extracting the specimen having a lumen through the subject's rectum.

7. The method of claim 6, wherein the step of extracting the specimen through the subject's rectum further comprises inserting the specimen into a transanally inserted endoscopic bag.

8. The method according to claim 6 further comprising:

intracorporeally forming an anastomosis between the proximal bowel portion and the distal bowel portion, wherein intracorporeally forming the anastomosis comprises transanally inserting a circular stapler and advancing the circular stapler through the distal bowel portion, the circular stapler comprising a stapling cartridge and an anvil component removably coupled thereto.

9. The method according to claim 6, wherein the step of extracting the specimen through the subject's rectum is accomplished without the specimen coming into contact with the bowel lumen.

10. The method according to claim 6, wherein the pre-formed adjustable fastening together with the length of suture is configured to form a loop around the edge portion of the distal bowl portion.

11. The method according to claim 6, wherein the pre-formed adjustable fastening detaches from within a shaft of the surgical device such that the pre-formed adjustable fastening is released between the first arm and the second arm.

12. The method of claim 6, wherein the step of extracting the specimen through the subject's rectum further comprises inserting a transrectal retractor into the distal bowel portion before insertion of the grasping tool and expanding the bowel wall.

* * * * *